US011783495B1

(12) United States Patent
Messmore et al.

(10) Patent No.: US 11,783,495 B1
(45) Date of Patent: Oct. 10, 2023

(54) METHODS AND APPARATUS FOR CALCULATING TORQUE AND FORCE ABOUT BODY JOINTS USING MACHINE LEARNING TO PREDICT MUSCLE FATIGUE

(71) Applicant: INSEER Inc., Iowa City, IA (US)

(72) Inventors: Mitchell Messmore, Iowa City, IA (US); Alec Diaz-Arias, Columbia, MO (US); John Rachid, Iowa City, IA (US); Dmitriy Shin, Columbia, MO (US); Jean E. Robillard, Iowa City, IA (US)

(73) Assignee: INSEER Inc., Iowa City, IA (US)

( * ) Notice: Subject to any disclaimer, the term of this patent is extended or adjusted under 35 U.S.C. 154(b) by 0 days.

(21) Appl. No.: 17/972,796

(22) Filed: Oct. 25, 2022

(51) Int. Cl.
*G06T 7/246* (2017.01)
*G06T 7/66* (2017.01)
(Continued)

(52) U.S. Cl.
CPC ............ *G06T 7/246* (2017.01); *A61B 5/1128* (2013.01); *A61B 5/4519* (2013.01); *A61B 5/4528* (2013.01); *A61B 5/7267* (2013.01); *A61B 5/7275* (2013.01); *G06T 7/0012* (2013.01); *G06T 7/66* (2017.01); *G06T 7/73* (2017.01);
(Continued)

(58) Field of Classification Search
CPC .... G06V 40/23; G06V 10/806; G06V 40/103; G16H 20/30; G06T 2207/20081; G06T 2207/20084; G06T 2207/30196; G06T 2207/10016
See application file for complete search history.

(56) References Cited

U.S. PATENT DOCUMENTS 9,566,004 B1 2/2017 Radwin et al.
10,032,352 B2 7/2018 Kozloski et al.
(Continued)

FOREIGN PATENT DOCUMENTS

WO  WO-2020210004 A1  10/2020

OTHER PUBLICATIONS

Looft, J. M. et al., "Modelling three-dimensional human strength capacity: logistic vs. polynomial surface equations," Int. J. Human Factors Modelling and Simulation, vol. 5, No. 1, 2015, pp. 5-18.
(Continued)

*Primary Examiner* — Diane M Wills
(74) *Attorney, Agent, or Firm* — COOLEY LLP

(57) ABSTRACT

An apparatus for calculating torque and force about body joints to predict muscle fatigue includes a processor configured to receive image frames depicting a subject. The processor is configured to execute at least one machine learning model using the image frames as an input, to generate a 2D representation of the subject, a subject mass value for the subject based on the 2D representation, and a 3D representation of the subject based on the 2D representation, where the 3D representation includes a temporal joints profile. The processor is further configured to compute each torque value for each joint of the subject from the 3D representation, based on the subject mass value. The processor is further configured to generate a muscle fatigue prediction for each joint of the subject, based on a set of torque values and a torque threshold.

19 Claims, 10 Drawing Sheets

(51) Int. Cl.
*G06T 7/73* (2017.01)
*G06T 7/00* (2017.01)
*G06T 11/00* (2006.01)
*G06T 17/00* (2006.01)
*A61B 5/11* (2006.01)
*A61B 5/00* (2006.01)

(52) U.S. Cl.
CPC .............. *G06T 11/00* (2013.01); *G06T 17/00* (2013.01); *G06T 2207/20081* (2013.01); *G06T 2207/20084* (2013.01); *G06T 2207/30196* (2013.01); *G06T 2210/12* (2013.01)

(56) References Cited

U.S. PATENT DOCUMENTS

| | | | |
|---|---|---|---|
| 10,096,230 | B2 | 10/2018 | Glynn |
| 11,328,239 | B2 | 5/2022 | Baek et al. |
| 11,482,048 | B1 | 10/2022 | Diaz-Arias et al. |
| 2009/0030767 | A1 | 1/2009 | Morris et al. |
| 2011/0054870 | A1* | 3/2011 | Dariush ............... G16H 50/50 348/46 |
| 2011/0199291 | A1 | 8/2011 | Tossell et al. |
| 2016/0070958 | A1 | 3/2016 | Whelan et al. |
| 2017/0169687 | A1 | 6/2017 | Kozloski et al. |
| 2017/0206431 | A1 | 7/2017 | Sun et al. |
| 2017/0296129 | A1 | 10/2017 | Petterson et al. |
| 2018/0014771 | A1 | 1/2018 | Merchant-Borna et al. |
| 2018/0024641 | A1 | 1/2018 | Mao et al. |
| 2018/0039745 | A1 | 2/2018 | Chevalier et al. |
| 2018/0255290 | A1 | 9/2018 | Holzer et al. |
| 2019/0012531 | A1 | 1/2019 | Radwin et al. |
| 2019/0012794 | A1 | 1/2019 | Radwin et al. |
| 2019/0138967 | A1 | 5/2019 | Akella |
| 2020/0178851 | A1 | 6/2020 | Singhose et al. |
| 2020/0273580 | A1 | 8/2020 | Kaszuba et al. |
| 2020/0327465 | A1* | 10/2020 | Baek ...................... G16H 20/30 |
| 2022/0001236 | A1* | 1/2022 | Mooney .................. G06F 18/00 |
| 2022/0237537 | A1 | 7/2022 | Baek et al. |
| 2022/0327775 | A1 | 10/2022 | Lee et al. |

OTHER PUBLICATIONS

"Upper Limb Localized Fatigue," ACGIH, 2016, 16 pages.

Dwivedi, P. "People Tracking using Deep Learning," Towards Data Science, Feb. 2019, [Online], Retrieved from the Internet: https://towardsdatascience.com/people-tracking-using-deep-learning-5c90d43774be, 5 pages.

Extended European Search Report for European Application No. 20788045.1, dated Dec. 5, 2022, 9 pages.

Herrington, L. et al., "The effect of patella taping on vastus medialis oblique and vastus laterialis EMG activity and knee kinematic variables during stair descent," J Electromyogr Kinesiol., Dec. 2005;15(6):604-607. doi: 10.1016/j.jelekin.2005.05.002.

International Search Report and Written Opinion for International Application No. PCT/US2020/023933, dated Aug. 20, 2020, 13 pages.

Office Action for U.S. Appl. No. 16/825,692, dated Feb. 1, 2021, 28 pages.

Office Action for U.S. Appl. No. 16/825,692, dated May 12, 2021, 27 pages.

Office Action for U.S. Appl. No. 16/825,692, dated Oct. 14, 2021, 37 pages.

Office Action for U.S. Appl. No. 17/717,714, dated Feb. 15, 2023, 6 pages.

* cited by examiner

METHODS AND APPARATUS FOR CALCULATING TORQUE AND FORCE ABOUT BODY JOINTS USING MACHINE LEARNING TO PREDICT MUSCLE FATIGUE

FIELD

The present disclosure generally relates to the field of machine learning and/or artificial intelligence. In particular, the present disclosure is directed to methods and apparatus for calculating torque and force about body joints using machine learning to predict muscle fatigue.

BACKGROUND

Workplaces often serve as labor-intensive environments that can lead to various types of workplace injuries. Musculoskeletal disorders are the most costly workplace injuries where complaints of back pain alone can cost employers more than 7 billion dollars annually and lead to more than 100 million lost workdays annually. These kinds of injuries contribute to loss of productivity and millions in annual health benefit payout costs. Musculoskeletal disorders can include repetitive stress injuries (RSIs) that comprise more than 100 different types of job-induced injuries, and are severe enough to inhibit simple activities with crippling and debilitating pain, potentially permanently impairing a worker's ability to perform job duties. Such injuries can result from (repetitive) improper lifting or manual lifting of heavy objects, lack of work breaks, or the like. RSIs are not limited to only manually taxing activities, but can also result from intensive keying, such as typing and clicking on a computer, causing strain to muscles and tendons of the human body.

In a large workplace, it is unrealistic to manually monitor every worker's movement throughout an entire work cycle or workday. As such, it is difficult to diagnose potential workplace injuries prior to an injury event for each and every worker. Video monitoring and analysis of video tapes are also tedious, time consuming, and inaccurate. A need exists to measure and predict potential workplace injuries or risk of injuries prior to an injury occurring.

SUMMARY

In one or more embodiments, an apparatus includes a processor and a memory operatively coupled to the processor. The memory stores instructions to cause the processor to receive a sequence of image frames where each image frame depicts a subject. The instructions further cause the processor to execute at least one machine learning model using the sequence of image frames as an input, to generate a 2D representation of the subject based on the sequence of image frames. The 2D representation includes a set of joint localization overlays and a set of limb segments. The at least one machine learning model further generates a subject mass value for the subject based on the 2D representation. The at least one machine learning model further generates a 3D representation of the subject based on the 2D representation, where the 3D representation includes a temporal joints profile. The instructions further cause the processor to compute each torque value from a set of torque values for a joint from a set of joints of the subject from the 3D representation, based on the subject mass value. The instructions further cause the processor to generate a muscle fatigue prediction for each joint from the set of joints of the subject, based on the set of torque values and a torque threshold.

In one or more embodiments, an apparatus includes a processor and a memory operatively coupled to the processor. The memory stores instructions to cause the processor to receive (1) a sequence of image frames via a sensor and (2) an object mass value of an object depicted in the sequence of image frames. Each image frame from the sequence of image frames depicts a subject moving an object. The instructions further cause the processor to execute at least one machine learning model using the sequence of image frames as an input. The at least one machine learning model generates a 2D representation of the subject based on the sequence of image frames, where 2D representation includes a set of joint localization overlays and a set of limb segments. The at least one machine learning model further generates a 3D representation of the subject depicting a set of poses based on the 2D representation, where the 3D representation include a temporal joints profile and a geometric representation of the object. The instructions further cause the processor to compute a total load force of the object during an action identified from the set of poses, based on the 3D representation and the object mass value. The instructions further cause the processor to generate a muscle fatigue prediction for the subject, based on the total load force of the object and a force threshold.

In one or more embodiments, a non-transitory, processor-readable medium stores processor-executable instructions to cause the processor to receive (1) a sequence of image frames via a sensor and (2) an object mass value of an object depicted in the sequence of image frames. Each image frame from the sequence of image frames depicts a subject moving an object. The instructions further cause the processor to execute at least one machine learning model using the sequence of image frames as an input, to generate a 2D representation of the subject based on the sequence of image frames. The 2D representation includes a set of joint localization overlays and a set of limb segments. The at least one machine learning model further generates a subject mass value for the subject based on the 2D representation. The at least one machine learning model further generates a 3D representation of the subject depicting a set of poses based on the 2D representation, where the 3D representation includes a temporal joints profile and a geometric representation of the object. The instructions further cause the processor to compute each torque value from a set of torque values for a joint from a set of joints of the subject from the 3D representation, based on the subject mass value. The instructions further cause the processor to compute a total load force of the object during a work cycle identified from the temporal joints profile, based on the object mass value. The instructions further cause the processor to generate a fatigue threshold based on the total load force and the set of torque values, to predict muscle fatigue. The instructions further case the processor to generate a customized force graph based on the muscle fatigue prediction.

DETAILED DESCRIPTION

Figure 1:
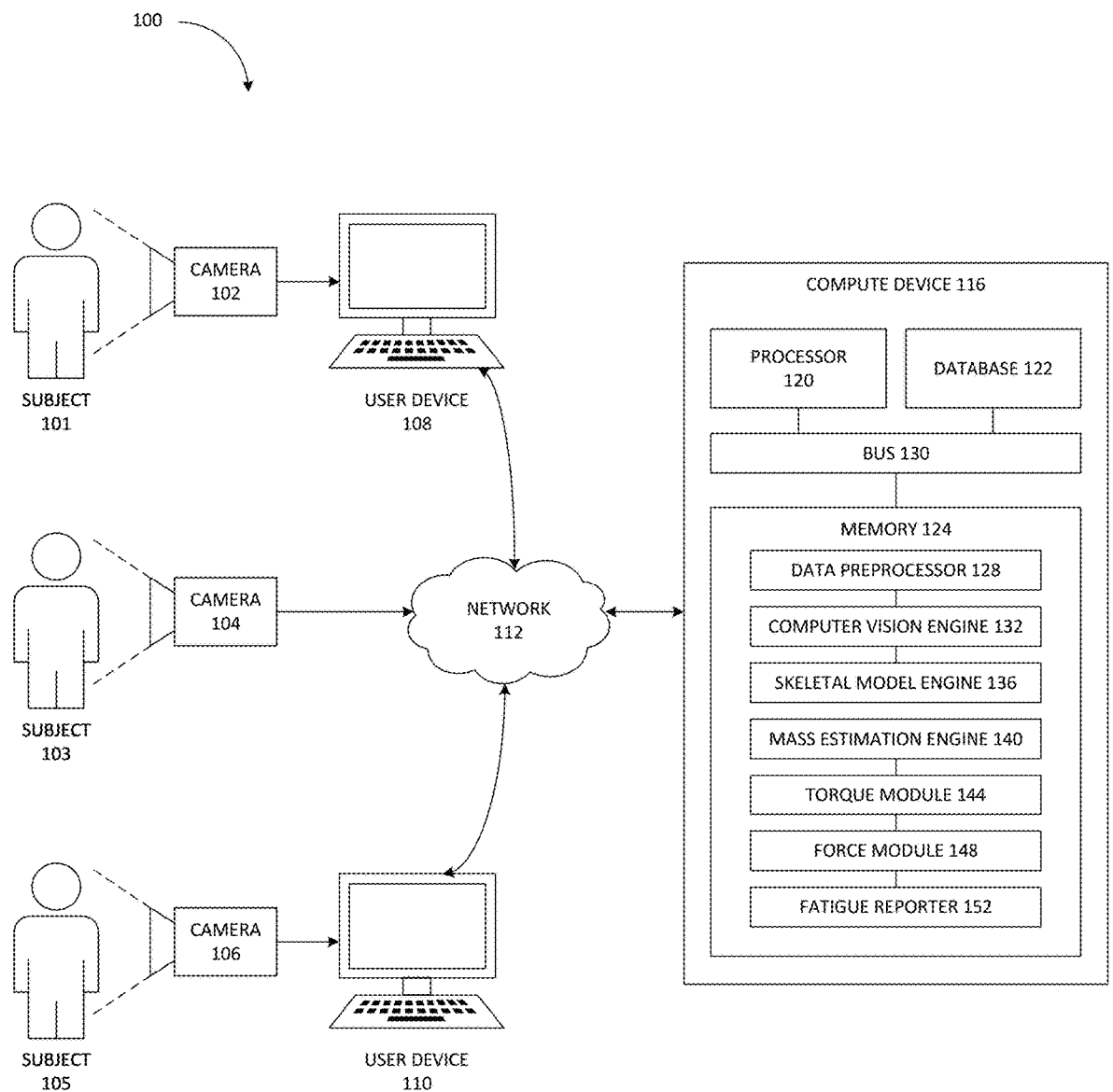
FIG. 1 is a block diagram of a system for calculating torque and force about body joints using machine learning to predict muscle fatigue, according to an embodiment.

In some embodiments, the present disclosure for calculating torque and force about body joints using machine learning to predict muscle fatigue can be separated into multiple sections: sensorless motion capture, human mass estimation, torque computation, force computation, muscle fatigue prediction, and graph generation. An apparatus incorporates computer vision and machine learning to receive a video input, calculate a mass (or weight) of the subject, and generate a 3D representation of a subject depicted in the video input. The apparatus can then compute a torque value about each of the subject's body joints and a total load/force exerted by the subject when performing an action (e.g., lifting, pulling, pushing, etc.). as depicted in the video input. The apparatus can then predict if the outputted torque values and total load or force indicates probable muscle fatigue about the subject, an action related to the muscle fatigue, and/or potential injury that may be a result of the muscle fatigue (or action performed).

At the sensorless motion capture section, the apparatus receives a video input depicting a subject (e.g., a person) or multiple subjects, and generates, using a machine learning model, a two-dimensional (2D) representation of the subject. The 2D representation can include a sequence of 2D skeletal figures that serves as a virtual representation of the subject. The 2D representation can include multiple 2D skeletal figures, each of which specifies the locations (e.g., 2D pixel locations) of the subject's bodily joints, limbs, body parts, and/or the like, in a 2D temporal space. In some implementations, the 2D representation can also include a sequence of image frames that includes a layer on top of the sequence of image frames; the layer including the sequence of 2D skeletal figures overlayed on the locations of the subject (or multiple subjects) in the sequence of image frames. The apparatus can use the machine learning model to first detect the subject (or multiple subjects) in each image frame extracted from the video input, and track the subject across each image frame. The apparatus can also use the machine learning model to generate a three-dimensional (3D) representation of the subject using the 2D representation. The 3D representation can include multiple 3D skeletal figures forming a sequence of poses performed by the subject, where each 3D skeletal figure includes multiple locations in a 3D space for each of the subject's joints, limbs, body parts, and/or the like (e.g., reconstruct 3D coordinates of the subject's joints, limbs, body parts, and/or the like, from their 2D pixel locations).

At the human mass estimation section, the apparatus uses the machine learning model to produce a mass value (also referred to as "weight") of the subject depicted in the video input. The machine learning model can include a convolutional neural network and/or transformer neural network that receives the 2D representation (or the 3D representation) and the image frames extracted from the video input to separate the subject depicted in each image frame from a background in each image frame, and to calculate the mass value of the subject. The mass value of the subject can include (or be) a weighted average of each mass value calculated for the subject in each image frame extracted from the video input.

At the torque computation section, the apparatus can compute a dynamic torque and a static torque for each of the subject's joints due to muscular, ligament, frictional, gravitational, inertial, and/or reaction forces acting on the joints of the subject. Using the 2D representation and/or the 3D representation (e.g., 3D joint locations) from the sensorless motion capture section and the mass value (e.g., mass of the subject) from the human mass estimation section, the apparatus can compute the dynamic torque and the static torque. The apparatus can also compute the dynamic torque and the static torque based on an inputted mass value of any objects held and/or moved by the subject depicted in the video input. The torque on the joints of the subject caused by the objects can be integrated into the computations for the dynamic torque and the static torque.

At the force computation section, in addition to computing torque about each joint of the body of the subject, the apparatus can also compute a total load (or force) value exerted by the subject when performing an action, such as, for example, lifting, pushing, moving, pulling, and/or the like, involving any objects.

At the muscle fatigue prediction section, the apparatus can produce a threshold for the torque (e.g., the dynamic torque and the static torque) to predict muscle fatigue. For instance, when the torque about joints of interest exceed a certain threshold for repetitive actions, the apparatus can predict muscle fatigue and/or generate a probability of muscle fatigue around the joints of interest (e.g., joints associated with the repetitive actions). The apparatus, using an equation (i.e., a model based on total load value (TLV), maximum voluntary contraction (MVC), and time (or percentage of time of a duty cycle of the joints of interest)), can determine an upper bound for safe torque values (and/or total load values exerted by the subject). The upper bound can indicate, for example, whether the torque values of the joints of the body of the subject are indicative of muscle fatigue, injury, and/or risk of muscle fatigue/injury. Any torque value and/or total load value exceeding the upper bound can be determined to be high risk for muscle fatigue, risk and/or the like.

At the graph generation section, the apparatus can output the results from the torque computation section, the force computation section, and/or the muscle fatigue prediction section. The outputs can be modeled via a customized graph to be displayed on an output device.

FIG. 1 illustrates a block diagram of a system 100 for calculating torque and force about body joints using machine learning to predict muscle fatigue, according to an embodiment. The system 100 includes a compute device 116, subjects (e.g., subject 101, 103, 105), cameras (e.g., camera 102, 104, 106, user devices (e.g., user device 108, 110), and a network 112. A subject 101, 103, 105 can include (or be) any person and/or persons. The subject 101, 103, 105 can be for example a user, a patient, a worker, or the like. The subject 101, 103, 105 also does not need to wear any motion sensors. (If the subject 101, 103, 105 wears a motion sensor, the data from the motion sensor is need not be used for the functions described herein.) The camera 102, 104, 106 can capture a video of the subject 101, 103, 105, to produce a sequence of image frames depicting each subject 101, 103, 105. Please note that while FIG. 1 shows three subjects 101, 103, 105, in certain instances and/or alternative embodiments, the number of subjects can be less than three or more than three.

The cameras (camera 102, 104, and/or 106) can include a sensor used to capture a physical phenomenon and output an electrical signal. For example, the sensor can include any one or more of a video camera, an image sensor, motion sensor, thermal sensor, biochemical sensor, pressure sensor, or the like. The sensor can also multiple sensors where each sensor is housed with each other in a sensor case (or housing or enclosure), forming a sensor suite. For instance a person can be moving across a field of view of the sensor, where the video generated by the sensor depicts the person in various locations across the sequence of image frames in the video. The video can be embodied in any electronic medium for recording, copying, playback, broadcasting, displaying, or the like. The video can include image frames forming the video. For example, a video having 60 frames per second can include 60 image frames for one second of the video. A video input of a person performing manual labor can include a sequence of image frames where each image frame contains an image of a pose the person is making while performing the manual labor (e.g., crouching to pick up a box on the ground, a squat stance to lift a heavy object on a platform, etc.). The sequence of image frames can depict, for example, a sequence of poses depicting the person performing an action. The video can also include, for example, a recorded 2D visual media of the person and its movements where the sensor is located at a fixed position.

As shown in FIG. 1, the camera 102 capturing a video of the subject 101 can be operatively coupled to the user device 108 and the camera 106 capturing a video of the subject 105 can be operatively coupled to the user device 110. The user device 108 and the user device 110 can connect to the network 112 to communicate with the compute device 116 and/or any other devices operatively coupled to the network 112. For instance, the user device 108, 110 can transmit the video depicting the subject 101, 105, respectively, to the compute device 116 via the network 112. In some cases, the compute device 116 can receive a video of a subject (subject 103) from a camera (camera 104) without passing through a user device. The compute device 116 can be operatively connected to multiple cameras and receive multiple videos depicting multiple subjects from different locations via a connection to the network 112 without passing through a user device. In some cases, the camera 102, 104, 106 can capture a video where the video depicts multiple subjects in each image frame from the video.

The compute device 116 can be configured to analyze the sequence of image frames of the video captured by the camera 102, 104, 106. The compute device 116 includes a processor 120 and a memory 124 that communicate with each other, and with other components, via a bus 130. The bus 130 can include any of several types of bus structures including, but not limited to, a memory bus, a memory controller, a peripheral bus, a local bus, a data bus, a control bus, and/or any combinations thereof, using any of a variety of bus architectures. The compute device 116 can be or include, for example, a computer workstation, a terminal computer, a server computer, a handheld device (e.g., a tablet computer, a smartphone, etc.), and/or any machine capable of executing a sequence of instructions that specify an action to be taken by that machine. The compute device 116 can also be or include multiple compute devices that can be used to implement a specially-configured set of instructions for causing one or more of the devices to perform any one or more of the aspects and/or methodologies of the present disclosure.

The compute device 116 can also include a network interface (not shown). A network interface device can be used for connecting the compute device 116 to one or more of a variety of networks and one or more remote devices connected thereto. Examples of a network interface device include, but are not limited to, a network interface card (e.g., a mobile network interface card, a LAN card), a modem, and any combination thereof. The compute device 116 can employ a wired and/or a wireless mode of communication.

Examples of a network 112 can be or include, for example, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and/or the like.

The processor 120 of the compute device 116 can be or include, for example, a hardware based integrated circuit (IC), or any other suitable processing device configured to run and/or execute a set of instructions or code. For example, the processor 120 can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. In some implementations, the processor 120 can be configured to run any of the methods and/or portions of methods discussed herein.

The memory 124 of the compute device 116 can be or include, for example, a random-access memory (RAM), a memory buffer, a hard drive, a read-only memory (ROM), an erasable programmable read-only memory (EPROM), and/or the like. In some instances, the memory can store, for example, one or more software programs and/or code that can include instructions to cause the processor 120 to perform one or more processes, functions, and/or the like. In some implementations, the memory 124 can include extendable storage units that can be added and used incrementally. In some implementations, the memory 124 can be a portable memory (e.g., a flash drive, a portable hard disk, and/or the like) that can be operatively coupled to the processor 120. The memory 124 can include various components (e.g., machine-readable media) including, but not limited to, a random-access memory component, a read only component, and/or any combinations thereof. The memory 124 can further include any number of program modules including, for example, an operating system, one or more application programs, other program modules, program data, and any combinations thereof.

The compute device 116 can also include a database 122. The database 122 can include (or be), for example, any data storage device, cloud database, local database, or the like. The database 122 can store any input and output received and generated by processes of the compute device 116. In some implementations, the compute device 116 can also include a database management system (DBMS) to interact with other devices (e.g., the user device 108, 110 and/or any output device). In some implementations, the user device 108, 110 can be structurally similar to the compute device 116. The compute device 116 can transmit a signal describing muscle fatigue prediction of the subject 101, 105 to the user device 108, 110 based on the video depicting the subject 101, 105.

Figure 2:
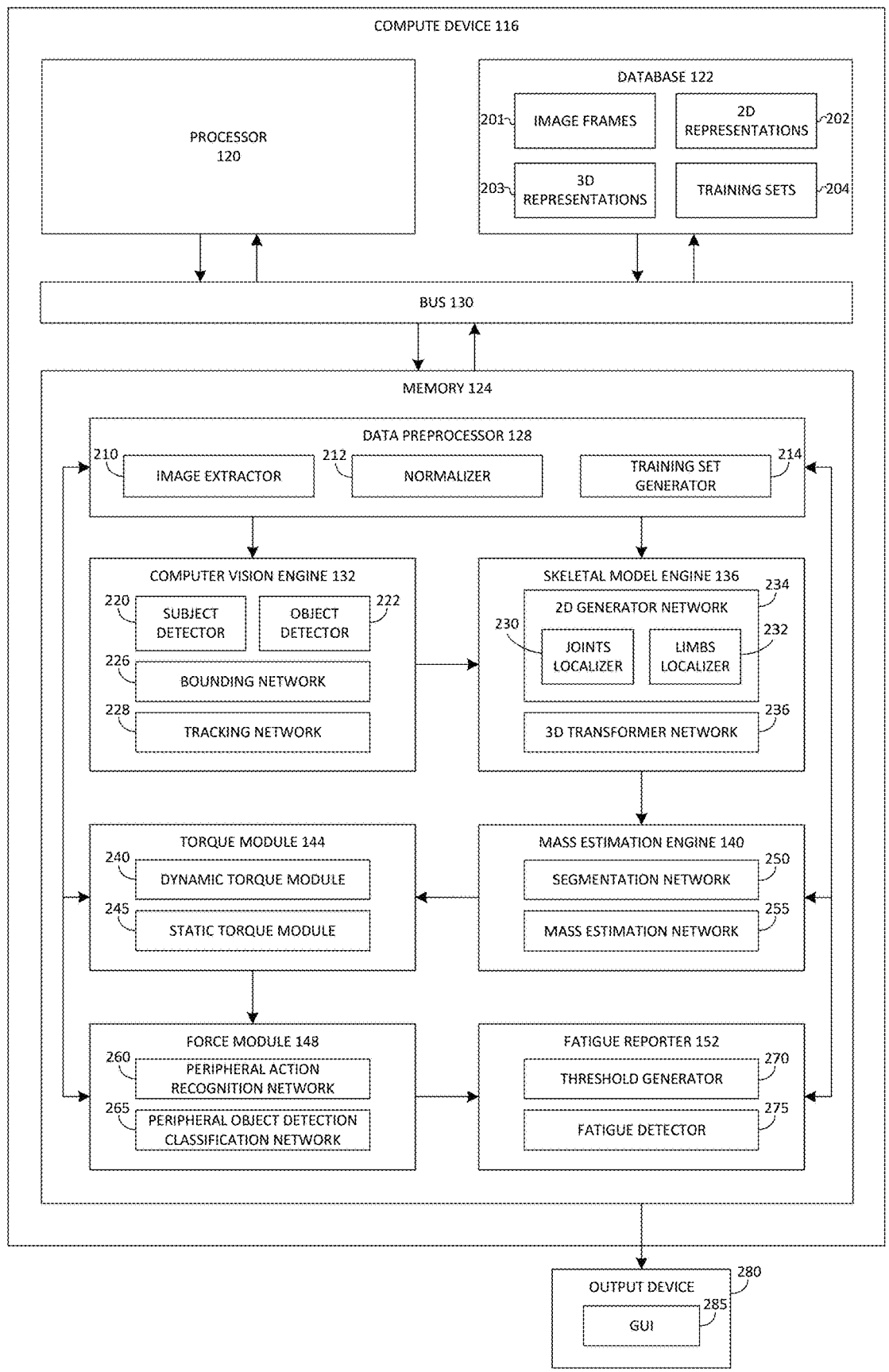
FIG. 2 is a block diagram of a compute device for calculating torque and force about body joints using machine learning to predict muscle fatigue, according to an embodiment.

FIG. 2 illustrates a block diagram of a compute device 116 for calculating torque and force about body joints using machine learning to predict muscle fatigue, according to an embodiment. The compute device 116 includes a processor 120, a database 122, a bus 130, and a memory 124 operatively coupled to the processor 120. The memory 124 of the compute device 116 can include a data preprocessor 128, a computer vision engine 132, a skeletal figure engine 136, a mass estimation engine 140, a torque module 144, a force module 148, and a fatigue reporter 152.

The database 122 of the compute device 116 can store and/or record any input/output received/generated by processes of the compute device 116. The database 122 can store, for example, sequences of image frames 201 (also referred to as "image frames") received from an input device (e.g., a camera) and/or image frames 201 extracted from a video received from the input device. The database 122 can store sets of 2D representations 202 (also referred to as "2D representations") of a subject depicted in the image frames 201. The database 122 can store sets of 3D representations 203 (also referred to as "3D representations") of the subject depicted in the image frames 201. The database 122 can store training sets 204 (also referred to as "training sets") used to train multiple machine learning models of the compute device 116. The database 122 is described in further detail in FIG. 3.

The data preprocessor 128 can receive a video captured from the input device such as, for example, a camera (not shown in FIG. 2), and extract a sequence of image frames 201 from the video. The data preprocessor 128 can include an image extractor 210, a normalizer 212, and a training set generator 214. The data preprocessor 128 can receive data including the video, video data, subject data, object data, and/or the like, from the camera, user inputs, and/or any other devices connected to the compute device 116. For example, in some instances, the data preprocessor 128 can receive a video depicting a subject (not shown in FIG. 2) from the camera. The data preprocessor 128 can be configured to extract data, select data to be analyzed, organize data, and/or normalize data, based on the video. For instance, the image extractor 210 can include a neural network to extract individual image frames 201 from the video. The normalizer 212 can normalize sequence of image frames 201 to a standardized (or preselected) size, format, brightness level, clarity level, and/or the like. The training set generator 214 can generate multiple types of training sets 204 based on the image frames 201 and/or any data used in the processes of the compute device 116. For instance, the training sets 204 can include, for example, data describing an image data type, a video data type, and/or the like, correlated to coordinate values representing joints, vectors representing limbs, and/or the like.

The data preprocessor 128 also receives an object mass value associated with an object depicted in the image frames 201. "Mass value" can also be referred to as "mass," "weight" or "weight value." For instance, the subject depicted in the image frames 201 can include a person carrying a heavy box (e.g., the object). The mass of the heavy box can be inputted manually for the data preprocessor 128 to associate the depicted heavy box with the inputted mass. This inputted mass (i.e., object mass value) can be, for example, a mass estimated by the user or otherwise input by a user. The object mass value can also be stored in the database 122, where the object mass value is associated with the object. In some implementations, the data preprocessor 128 can receive demographic data about the subject. The demographic data can include, for example, age, gender, ethnicity, occupation, and/or any information about the subject.

The computer vision engine 132 can be executed by the processor 120 to detect the subject depicted in the image frames 201, detect the object depicted in the image frames 201, track the subject and the object across the image frames 201, and/or classify the subject and object depicted in the image frames 201. The computer vision engine 132 can include a subject detector 220, an object detector 222, a bounding network 226, and a tracking network 228. The computer vision engine 132 can include at least one machine learning model. The machine learning model can include a neural network, a convolutional neural network (CNN), a transformer neural network, a hybrid neural network, an unsupervised machine learning model, a supervised machine learning model, and/or the like. The memory 124 can store multiple machine learning models, neural networks, and/or any combination thereof.

The subject detector 220 can identify the subject depicted in the image frames 201. The subject detector 220 can also detect multiple subjects depicted in the image frames 201. The object detector 222 can identify the object involved with the subject depicted in the image frames 201. For instance, the object can include a box that the subject is carrying, a cart that the subject is pushing, a lever that the subject is pulling, or the like. The bounding network 226 can include (or be) a machine learning model, neural network, and/or a CNN. The bounding network 226 can be configured to generate a bounding overlay that outlines the subject depicted in the image frames 201. In some implementations, the bounding overlay can be invisible and/or not directly overlayed on an associated image frame to be viewed by a user. The bounding network 226 can also generate a bounding overlay (not shown in FIG. 2) for each subject where multiple subjects are depicted in the image frames 201. The bounding network 226 can generate a set of bounding overlays associated with the same subject depicted throughout the image frames 201. The bounding overlay can include a virtual box outlining the subject in each image frame. The bounding overlay can include temporal joint data of the subject including the dimensional location of a recognizable human subject as the location shifts following the movements (or location) of the human subject captured across the image frames 201. In some cases, the temporal joint data can include 2D coordinates of the corners of the bounding overlay outlining the subject. (The bounding overlay is further described in detail in FIG. 5).

The tracking network 228 of the computer engine 132 can be executed by the processor 120 to match the bounding overlay in the image frame to the bounding overlay of a previous image frame. The tracking network 228 can include any machine learning model, neural network, or the like. The tracking network 228 can generate, using the bounding overlay from the set of bounding overlays as an input, a dimensional feature vector from a set of dimensional feature vectors (also referred to as "dimensional vectors") for each bounding overlay from the set bounding overlays. For instance, the tracking network 228 can include a feature extractor to identify an appearance of the subject in each bounding overlay into the dimensional feature vector. The dimensional feature vectors can be compared with each other via the tracking network 228 to match the subject outlined by the bounding overlay in the previous image frame to the next image frame. The dimensional feature vector can include measurable characteristics such as, for example, height of the subject, patterns associated with the subject, and/or numerical features describing the subject (e.g., 2D pixel locations and/or coordinates of the subject, parts of the subjects, the object, etc.). In some implementations, the processor 120 can generate a subject identifier for the subject identified in the image frames 201 via the tracking network 228. The processor 120 can generate a set of subject identifiers for each subject detected in the image frames 201, to reduce computational overhead in locating, identifying, and tracking the subject across different videos, new videos, or when the subject is absent in some image frames from the sequence of image frames 201.

The skeletal figure engine 136 can be executed by the processor 120 to generate 2D representations 202 and/or 3D representations 203 based on the identification of the subject from the computer vision engine 132 (e.g., the subject identifier). The skeletal figure engine 136 can include a 2D generator network 234 and a 3D transformer network 236. The skeletal figure engine 136 can include any number of machine learning models and/or neural networks. The 2D generator network 234 can include a joints localizer 230 and a limbs localizer 232. The 2D generator network 234 can be executed by the processor 120 to generate a 2D representation of the subject across the sequence of image frames 201. The joints localizer 230 can be configured to generate a set of 2D locations of each joint of the body of the subject. The joints localizer 230 can include (or be) any machine learning model and/or neural network. A 2D location from the set of 2D locations can include, for example, 2D coordinates and/or 2D pixel locations for each joint of the body of the subject. The joints localizer 230 can map each joint from the body of the subject with a virtual representation for each joint. The joint can include, for example, a knee, a wrist, an elbow, an ankle, or the like. The joint localizer 230 can generate a joint localization overlay from a set of joint localization overlays for each image subject depicted in each image frame from the sequence of image frames 201, using the sequence of image frames 201 as an input. The joint localization overlay can also be generated based on the set of 2D locations of the set of joints of the body of the subject. The joint localization overlay can be consistent with the joint localization overlay of U.S. patent application Ser. No. 17/740,650, dated May 10, 2022, and entitled, "METHODS AND APPARATUS FOR HUMAN POSE ESTIMATION FROM IMAGES USING DYNAMIC MULTI-HEADED CONVOLUTIONAL ATTENTION," which is incorporated in its entirety herein for all purposes. The joint localization overlay can include, for example, a map of the set of joints of the body of the subject. The map of the set of joints can depict how where each joint is located on the body of the subject based on the sequence of image frames 201. In some implementations, the joint localization overlay can include a heat map (e.g., a 2D probability distribution) describing the 2D locations of the set of joints of the subject outlined by the bounding overlay. The joints localizer 230 can use a nonmaximal suppression max finder technique to extract specific joint locations from a set of heat maps as local maximums that exceed a fixed threshold value indicating each joint across the sequence of image frames 201. The joints localizer 230 can also generate multiple joint localization overlays for multiple subjects depicted in the sequence of image frames 201 where each subject is associated with a unique subject identifier. In some implementations, multiple joint localization overlays can include (or form) a map of the set of joints of the body of the subject across the sequence of image frames 201.

The limbs localizer 232 can be configured to generate a limb localization overlay from a set of limb localization overlays based on the joint localization overlay from the set of joint localization overlays associated with the subject for each image frame from the sequence of image frames 201. The limbs localizer 232 can include (or be) any machine learning model and/or neural network. The limb localization overlay can include a map that connects the set of joints from the joint localization overlay associated with an image frame, forming limb segments that represent body parts of the subject. In some implementations, the limb localization overlay can include a map of the set of joints and the set of limbs of the body of the subject. The map can include representations for the set of limbs and the set of joints, where the representations for the set of limbs can connect each joint accordingly, depicting body parts of the subject. Multiple limb localization overlays can include (or form) multiple maps of joints and limbs for each image frame from the sequence of image frames 201. The limbs localizer 232 can generate each map across the sequence of image frames 201. The limb localization overlay can include (or be) a 2D vector field (e.g., a partial affinity field) for each body part (e.g., limbs) that connects each joint from the set of joints of the subject, to form a 2D skeletal figure of the subject. The partial affinity field of a set of partial affinity field associated with each image frame from the sequence of image frames 201 can be used to match each joint from the set of joints associated with each image frame to create the 2D skeletal figure of a sequence of 2D skeletal figures for the subject across the sequence of image frames 201.

In some implementations, the 2D generator network 234 can generate a matching score for each pair of joints defining a body part (e.g., a limb segment, such as an arm, torso, leg, forearm, etc.). The matching score can be computed as follows u, v can denote a 2D pixel location of a right wrist joint and a right elbow joint, respectively. The matching score of u and v is the integral of a dot product of a 2D vector field (i.e., a partial affinity field) for a right forearm flowing between the right elbow joint and the right wrist joint, against a unit vector from u to v. The notation can include:

$$\oint_u^v {}_u \gamma(f \cdot w)$$

where $\gamma$ is a parametrization of the line connecting u and v, f is the partial affinity field for the right forearm, and w is the unit vector in the direction from u to v. After computing a set of matching scores for all pairs of right wrist and right elbow across the sequence of image frames 201, the processor 120 can match the pair of joints using the Munkres Matching Algorithm. In some implementations, additional post processing is applied to group all matched body parts to create the 2D skeletal figure from the sequence of 2D skeletal figures. The processor 120 can compare the 2D skeletal figure for the subject associated with an image frame against the bounding overlay outlining the subject based on the subject identifier, to establish a 2D skeletal identifier for 2D skeletal figure. The processor 120 can perform the above process for each image frame from the sequence of image frames 201.

The sequence of 2D skeletal figures produced based on the set of limb localization overlays and/or the set of joint localization overlays can form the 2D representation of the subject across the sequence of image frames 201. The 2D representation can be further described in detail with respect to FIG. 6, which is discussed below. The limb localization overlay and/or the joint localization overlay can be further described in detail with respect to FIG. 7, which is discussed below. The 2D skeletal figure can be overlayed on the image frame as shown in FIG. 7. The 2D generator network 234 can generate a set of 2D representations 202 for multiple subjects depicted in various videos, and stored in the database 122. In some implementations, the 2D representation can also include a sequence of image frames that includes a layer on top of the sequence of image frames 201 extracted from the video input. The layer can include the sequence of 2D skeletal figures overlayed on the locations of the subject (or multiple subjects) in the sequence of image frames 201.

The 3D transformer network 236 can be executed to generate a 3D representation of the subject depicted in the sequence of image frames 201, based on the 2D representation from the 2D generator network 234. The 3D transformer network can include (or be) any machine learning model and/or neural network. In some instances, the 3D transformer network can be consistent with the ConvFormer module described in U.S. patent application Ser. No. 17/740, 650. The 3D transformer network 236 can receive the 2D representation as an input and generate a sequence of 3D skeletal figures (e.g., 3D reconstructions of the 2D skeletal figures) forming the 3D representation of the subject depicted in the sequence of image frames 201. Each 3D skeletal figure can outline the set of joints and connecting limb segments (or body parts) of the subject depicted in each image frame. The 3D skeletal figure can be overlayed on the image frame, thereby producing an outline of the subject's skeletal framework on top of the subject depicted in the image frame. This is so, at least in part, to identify the subject's pose and/or movement in a sequence of time.

The sequence of 3D skeletal figures forming the 3D representation of the subject can be used to estimate the movement and location of each 3D skeletal figure from the sequence of 3D skeletal figures in a 3D space. The 3D skeletal figure can depict a pose that the subject is performing at a given image frame. For instance, the 3D transformer network 236 can estimate a set of 3D joint locations and/or 3D limb locations in the 3D space based on the 2D skeletal figure found in the image frame. The 3D transformer network 236 can perform the estimations described above for each image frame from the sequence of image frames 201. In some implementations, the 3D transformer network 236 can include (or be) a convolutional neural network, where the processor 120 can use various convolutional filters of various sizes to reduce complexity between image frames to reconstruct the 3D representation of the subject.

The 3D transformer network 236 can also generate a temporal joints profile for each joint of the set of joints of the subject. The temporal joints profile can be consistent with the temporal joints profile described in U.S. patent application Ser. No. 17/740,650. The temporal joints profile can be, for example, a sequence of a joint from a sequence of 3D skeletal figures depicting 3D poses of the subject based on the sequence of image frames 201. The temporal joints profile can be described in further detail with respect to FIG. 9, which is discussed below. In an example, a temporal joints profile for a right wrist can depict the 3D locations (e.g., 3D coordinates) of the right wrist in a 3D space by connecting the locations of the right wrist in each 3D skeletal figure associated with each image frame in the sequence of image frames 201. The 3D transformer network 236 can generate a complete set of temporal joints profiles for each joint of the body of the subject. In some implementations, generating the 3D representation and/or the temporal joints profile can include generating a set of frame interrelations using the 2D representation and a time sequence as inputs, to produce the 3D representation, the plurality of frame interrelations including a sequence of the 3D poses in a 3D space. The frame interrelation can include, for example, a frame-wise relation and/or sequence between two or more image frames (or two or more consecutive image frames) from the sequence of image frames 201. In some cases, the frame interrelation of a set of image frames 201 can include a representation of a path traveled by a joint in the 3D space between two or more 3D skeletal figures. In some implementations, the 3D transformer network 236 can extract a set of scaled frame interrelations based on a convolutional filter size, prior to generating the 3D representation. The convolutional filter size can be, for example, a 2D kernel size for which convolutional layers are to follow. The convolutional filter size can be used to adjust the level of sparsity to be applied for the set of frame interrelations, resulting in the set of scaled frame interrelations. The convolutional filter size can be used to reduce complexity and/or computational overhead in generating the 3D representation.

The memory 124 includes the mass estimation engine 140 where the mass estimation engine 140 can be executed by the processor 120 to generate a subject mass value based on the 2D representation and/or the 3D representation via the skeletal figure engine 136. In some implementations, the mass estimation engine 140 can be configured to also receive the sequence of image frames 201 as an input to produce an accurate body mass estimation (e.g., the subject mass value) of the subject (or multiple subjects) detected in the sequence of image frames 201. The mass estimation engine 140 can include (or be) any number of machine learning models and/or neural networks, CNNs, transformer neural networks, hybrid neural networks, and/or the like. For instance, the mass estimation engine 140 can include a segmentation network 250 and a mass estimation network 255. The segmentation network 250 can include (or be) any machine learning model and/or neural network. The segmentation network 250 can receive the 2D representation and/or the 3D representation, and separate the subject detected in each image frame from the sequence of image frames 201 from a background in each of those image frames. The segmentation network 250 can extract, from each image frame depicting the subject in the 2D representation and/or the 3D representation, the subject detected, where the mass estimation network 255 can be configured to receive the extracted subject from each image frame and generate the subject mass value of the subject. The subject mass value can include, for example, a single numerical value describing the mass and/or weight of the subject and/or multiple subjects depicted in the sequence of image frames 201. The mass estimation network 255 can include (or be) any machine learning model and/or neural network. In some implementations, the segmentation network 250 and the mass estimation network 255 can receive, as inputs, a subset of image frames from the sequence of image frames 201, where the subset of image frames include image frames where the subject is present and/or depicted.

In some implementations, the subject mass value can include a weighted average of constant subject mass values. For instance, the segmentation network 250 can separate the subject from the background for each image frame from the subset of image frames and the mass estimation network 255 can track the subject (e.g. track the subject via the bounding overlay and/or the subject identifier), and perform a weighted average of a set of subject mass values calculated for the subject in each image frame from the subset of image frames depicting the subject. For instance, the mass estimation network 255 can assign, for each image frame that depicts the subject, a constant subject mass value for the subject. The mass estimation network 255 can assign constant subject mass values for multiple subjects depicted in each image frame from the subset of image frames and apply a weighted average of a set of constant subject mass values to generate the subject mass value for the subject.

The memory 124 can include the torque module 144 that can be configured to receive the subject mass value and compute a set of torque values for each joint of the body of the subject from the 2D representation and/or the 3D representation. In some implementations, the torque module 144 can include a dynamic torque module 240 configured to compute a dynamic torque value from a set of dynamic torque values for each joint from the set of joints, and a static torque module 245 configured to compute a static torque value from a set of static torque values for each joint from the set of joints. Given a video of a subject or multiple subjects, the torque module 144 can compute torque values (e.g., a dynamic torque and a static torque) about one or more of the subject's (or subjects') joints due to muscular, ligament, frictional, gravitational, inertial, and/or reaction forces acting on the set of joints of the body of the subject (or bodies of the subjects). The torque module 144 can receive (1) a set of 3D locations from the 3D representation of the subject and (2) the subject mass value of the subject, and/or (3) the object mass value of any object involved with the subject (e.g., object held by the subject, object moved by the subject, etc.). The object mass value can be provided, for example, as an input manually. As such, the torque values (e.g., the dynamic torque and the static torque) of the set of joints engaged with the object (e.g., joints of interest) can be updated based on the object mass value and/or location of the object.

To compute a torque value about a joint of interest (e.g., a joint of set of joints engaged with the object), the dynamic torque module 240 can compute a moment of inertia about the joint caused by a body part and/or object that is connected, engaged, and/or held by the subject. For each body part and/or object, the equation to compute the torque value from a set of torque values for the joint from the set of joints can follow:

$$torque = L*W + M*A + I*\alpha$$

where L represents a torque arm (the distance between the center of mass (CoM) of the object or body part and the joint of interest), M represents a mass value of a limb segment and/or body part engaged with the object, A represents a linear acceleration value of the CoM of the limb, I represents a torque inertia value, and $\alpha$ represents an angular acceleration value of the limb segment with respect to a ground plane. In some implementations, the dynamic torque module 240 can perform numerical differentiation on the 3D representation to produce the linear acceleration value and the angular acceleration value for each limb segment (or body part) from the set of limb segments of the subject, to compute each torque value for each joint. The set of torque values of all interacting body parts and objects can be computed and summed to obtain a total dynamic torque about the joint. In some cases, the torque value about each joint of interest can be associated with a set of body parts that are engaged with the joint of interest when moving the object and/or performing an action. For instance, computing the torque value about a back joint (e.g., L5/S1) includes computing a set of moments of inertia for a right/left upper arm, right/left forearm, torse, head, and/or the object. In another example, computing the torque value about the right/left shoulder can include computing a set of moments of inertia for the right/left upper arm, right/left forearm, and/or the object. In another example, computing the torque value about the right/left elbow can including computing a set of moments of inertia for the right/left forearm and/or the object.

The static torque module 245 can compute the static torque about the joint by removing acceleration in the equation above. In some implementations, the static torque module 245 can be configured to calculate the torque value for joints based on actions performed by the subject that produce reactive forces (e.g., pushing a door). In some implementations, the dynamic torque module 240 can be configured to calculate the torque value for joints based on actions performed by the subject that produce rotational forces.

In some implementations, the torque module 144 (including the dynamic torque module 240 and the static torque module 245) can receive mass values for each limb from the set of limbs of the subject from population-based models depending on age, gender, ethnicity, and/or the like. In some cases, the mass values for each limb can also include center mass values (e.g., CoM value for each limb). The center mass values can also be referred to as "center of mass values." For example, in a workplace of Caucasian male workers, a worker's mass can be input into Dempster's equations to obtain estimates for each body part's weight. In some implementations, the torque module 144 can be configured to generate a center of mass value of each body part from the set of body parts of the subject based on the 3D representation and/or the subject mass value. The center of mass value can include a numerical value describing a distribution of mass in space (e.g., the 3D space and/or the 2D space) where the weighted relative position of the distributed mass sums to zero. In some implementations, the torque module 144 can detect the center of mass value of each limb and/or body part associated with the object based on the 3D representation of the subject and generate a body part model of the body part associated with the object. The body part model can include, for example, a representation of the body part. The body part model can also include a geometric representation of the object. For instance, the geometric representation can be a simplified virtual representation of the object, such as, for example, a rectangular prism, a sphere, a cylinder, a cone, or the like, based on a shape of the object. For example, the object can be a toolbox and the geometric representation can be a rectangular prism. The body part model and the geometric representation of the object can be overlayed on the 3D representation.

The memory 124 includes the force module 148 configured to compute a total load force (or force exerted) by the subject depicted in the sequence of image frames 201 (or each subject from multiple subjects) while performing an action. The total load force (also referred to as "total force") can include (or be) a numerical value. The action can include, for example, lifting, pushing, pulling, and/or any combination thereof. For instance, computing a lifting force (e.g., the force required to lift a box from ground onto a table) involves the user to input the mass of the object to be lifted, the hand(s) of the subject involved to lift the object, and a video of the subject completing the lifting of the object. The processor 120 and/or the force module 148 can detect that the lifting force is due to be computed by manual user input or using a peripheral action recognition network

260. The peripheral action recognition network 260 can include (or be) any machine learning model and/or neural network, and be configured to detect and/or predict a future pose and/or set of future poses of the subject. In some cases, the peripheral action recognition network 260 can also detect and/or predict the body parts, joints, and/or limb segments that will be engaged, utilized, and/or moved based on the object (e.g., object trajectory, object 3D locations, object linear acceleration, object mass value, etc.).

In some implementations, the force module 148 can also include a peripheral object detection classification network 265. The peripheral object detection classification network 265 can include any machine learning model and/or neural network, and configured to identify the object mass value and the subject's handedness (preferential use of one hand). For instance, the peripheral object detection classification network 265 can receive the sequence of image frames 201 and/or the 3D representation including the geometric representation of the object as inputs to compute the object mass value of the object and determine whether the subject is right-handed, left-handed, or ambidextrous. The peripheral object detection classification network 265 can also assign the handedness of each subject detected from the sequence of image frames 201 by assigning a classification for handedness to each subject identifier. In some cases, the peripheral object detection classification network 265 can also determine which hand (right or left) the subject might use to engage with the object based on the subject's handedness classification. In some cases, the peripheral object detection 265 can also place different thresholds indicating safe exertion of force and/or movement of joints based on the handedness. For instance, a worker who is right-handed may have greater tolerance, strength, and/or mobility with right arm movements with an object compared to using the left arm.

In some cases, a total observed force applied to the object being lifted can be calculated using a standard force equation:

$$\vec{F}=m\vec{\alpha}$$

where $\vec{F}$ denotes the total force, m denotes the mass of the object (e.g., the subject mass value), and $\vec{\alpha}$ denotes a 3D acceleration of the object being lifted. There are two main forces of interest acting on the object at the time of the lift: a human force $\vec{H}$ applied in an upward direction and a gravitational force on the box $\vec{G}$ in a downward direction. The gravitational force is computed as:

$$\vec{G}=mg\vec{z}$$

where g is 9.8 m/s² (the gravitational constant on Earth) and $\vec{z}$ is a unit vector that points from the center of mass of the box to the center of mass of the Earth. The total force is approximately the net force of the gravitational force and the applied force exerted by the subject:

$$\vec{F}=\vec{H}+\vec{G}$$

And hence the lifting force applied by the subject can be solved for as:

$$\vec{H}=\vec{F}-\vec{G}=m(\vec{\alpha}-g\vec{z})$$

In some instances, the acceleration of the object being lifted d can be an unknown quantity. The force module 148 can compute $\vec{\alpha}$ as the acceleration of the center of mass (CoM) of the object. For instance, the CoM of the object can move in parallel with the hand(s) of the subject making contact with the object. The skeletal figure engine 136, including the 3D transformer network 236, can extract 3D locations, such as, for example, 3D coordinates of the hand(s) of the subject in each image frame from the sequence of image frames 201. The 3D coordinates can also form location vectors for the hand(s) and/or any extending body part of the subject. The force module 148 can use a central difference method for discrete derivatives and the location vectors of the hand(s) to compute the acceleration of the hand(s). As such, the acceleration of the hand(s) is the acceleration of the object being lifted, using the equation:

$$\vec{H}=m(\vec{\alpha}-g\vec{z})$$

to produce the total force applied to the object. A magnitude of the total force can also be a quantity of interest, which is output as a function of time t (in frames or seconds):

$$M(t):=|\vec{H}(t)|=\sqrt{H_x(t)^2+H_y(t)^2+H_z(t)^2}$$

The above method for computing total force for lifting can be identical for computing total force for pushing. For instance, a push force describes the force applied by a subject to an object either that will slide along a surface or an object residing on a cart with wheels. In some cases, the force module 148 can compute the total force in 3D (e.g., using 3D locations, 3D coordinates, location vectors, etc.). However, the force module 148 can also use vector components (e.g., dimensional feature vectors, limb segments, 2D pixel locations, 2D coordinates, etc.) in the 2D space that is parallel to the surface that the object is sliding along. The net force on the object is given by:

$$\vec{F}=m\vec{\alpha}$$

where $\vec{F}$ denotes the total force, m denotes the mass of the object, and $\vec{\alpha}$ denotes the 3D acceleration of the object being pushed. There are two main forces of interest acting on the object at the time of the push: the human force $\vec{H}$ applied in a direction of the push and a frictional force between the surface and the object $\vec{K}$.

$$\vec{K}=mg\vec{z}$$

where g is 9.8 m/s² (the gravitational constant on Earth) and $\vec{z}$ is a unit vector that points from the center of mass of the box to the center of mass of the Earth. The total force can be approximately the net force of the gravitational force and the human applied force:

$$\vec{F}=\vec{H}+\vec{G}$$

And hence the lifting force applied by the subject can be solved similarly to the solving the lifting force for as described above:

$$\vec{H}=\vec{F}-\vec{G}=m(\vec{\alpha}-g\vec{z})$$

As such, the force module 148 can use the central difference method for discrete derivatives and the location vectors of the hand(s) to compute the acceleration of the hand(s). As such, the acceleration of the hand(s) is the acceleration of the object being lifted, using the equation:

$$\vec{H}=m(\vec{\alpha}-g\vec{z})$$

to produce the total force applied to the object. A magnitude of the total force can also be a quantity of interest, which is output as a function of time t (in frames or seconds):

$$M(t) := |\vec{H}(t)| = \sqrt{H_x(t)^2 H_y(t)^2 + H_z(t)^2}$$

The memory 124 includes the fatigue reporter 152, where the fatigue reporter 152 can be executed by the processor 120 to generate a muscle fatigue prediction for each joint from the set of joints of the subject based on the set of torque values and/or the total load force (also referred to as "force" or "load") exerted by the subject (on the object). The fatigue reporter 152 can include any computer hardware/software module as described herein. The muscle fatigue prediction can include (or be) a prediction of whether the subject indicates a likelihood of muscle fatigue, based on the set of torque values for the set of joints of the subject and/or the total load force applied by the subject. For instance, a series of torque values for each 2D/3D skeletal figure across the sequence of image frames 201 can reveal a decrease in joint movement, acceleration, rotation, and/or the like, indicating that the subject is fatigued, parts of the body is fatigued or stressed, and/or parts of the body is injured or likely to get injured.

The fatigue reporter 152 can include a threshold generator 270 and a fatigue detector 275. For instance, the fatigue detector 275 can also generate the muscle fatigue prediction based on a fatigue threshold generated by the threshold generator 270, indicating safe torque values and/or total load force for actions (or repetitive actions) performed by the subject. The threshold generator 270 can be configured to generate the fatigue threshold that sets an upper bound for calculations (e.g., torque values, location vectors, joint paths, total load force, object mass value, subject mass value, etc.) that when exceeded, indicates a likelihood of muscle fatigue. The fatigue threshold can include a torque threshold and a force threshold. The torque threshold can include (or be) an upper bound for torque values that when a torque value exceeds the upper bound, the joint associated with that torque value is deemed high risk for muscle fatigue. In some cases, the torque threshold can include multiple thresholds for different joints of a human body. For instance, the torque value produced by a right elbow can be greater in range than the torque value produced by a right wrist. The threshold generator 270 can generate and/or set individual joint torque thresholds for each joint of the body of the subject. The torque threshold (including the individual joint torque thresholds) can be manually adjusted and/or modified by a user. The force threshold can include (or be) an upper bound for the total load force exerted by the user that when a total load force exceeds the upper bound, the applied total load force to perform the action associated with that total load force is deemed high risk for muscle fatigue. In some cases, the force threshold can include multiple thresholds for different actions (e.g., lifting, pulling, pushing, etc.) of a human body. For instance, the total load force produced by a lifting action can be greater in range (or different) than the total load force produced by a pushing action. The threshold generator 270 can generate and/or set individual force thresholds for different actions and/or areas of the body (e.g., center of mass) involved with an action and/or an action involving an object. The force threshold (including the individual force thresholds) can be, for example, manually adjusted and/or modified by a user. In some implementations, the threshold generator 270 can assign unique fatigue thresholds (torque thresholds and force thresholds) for different subjects by assigning the unique fatigue thresholds to each subject identifier.

In some implementations, the threshold generator 270 can use an equation, i.e., a model based on total load value (TLV), maximum voluntary contraction (MVC), and time (or percentage into a work cycle) to determine the fatigue threshold for safe torque values and/or safe load values that are less likely to result in muscle fatigue about the subject. The equation below is expressed in terms of normalized torque or load, which can be obtained by dividing by the maximum possible value (MVC) of load or force:

$$MVC = (100\%) \cdot \left(-0.143 \ln\left(\frac{DC}{100}\right) + 0.066\right)$$

where DC is the percentage of time over a work cycle or a certain time period that force is applied. The above equation can be used to express the maximum safe amount of force exerted on a joint at a given time in the work cycle in a context of repetitive tasks. Repetitive tasks can include, for example, typing on a keyboard, moving up and down a ladder, stacking multiple items in an inventory, or the like. Repetitive actions can include multiple iterations of various tasks or tasks where breaks are present in between the same tasks.

In some implementations, the fatigue detector 275 can generate the muscle fatigue prediction based on a work cycle. For instance, the skeletal figure engine 136, including the 2D generator network and/or the 3D transformer network, can identify image frames from the sequence of image frames 201 depicting the subject performing an action. A period in time and/or a subset of image frames from the sequence of image frames 201, where the subject is depicted to be performing an action, can be denoted as the work cycle. The work cycle can also be, for example, a time period in which the subject is performing a laboring action. In some implementations, the torque module 144 and/or the force module 148 can compute torque values for the set of joints and/or the total load force exerted by the subject during the work cycle identified from the temporal joints profile of the 3D representation of the subject, based on the object mass value. The work cycle can be a period of the actions performed by the subject that include laboring (e.g., lifting an object, pushing an object, pulling an object, etc.). The work cycle can also be, for example, a subset of image frames from the sequence of image frames 201 where the subject is depicted laboring. For instance, the subject depicted in the sequence of image frames 201 can be taking a break for most of the image frames, while the remainder of image frames depicts the subject pushing a cart from one location to another. The image frame depicting the subject beginning to push the cart to the image frame depicting the subject finishing the pushing of the cart can be denoted as a work cycle. The work cycle can also be, for example, a sequence of poses including a beginning pose and an end pose depicting the start and finish of the subject completing a laboring action. The fatigue detector 275 can detect a time sequence of the work cycle, to generate the muscle fatigue prediction of the subject during the time sequence associated with the work cycle. In some instances, the sequence of image frames can depict multiple work cycles or multiple different work cycles where the subject is performing repetitive tasks or a variety of tasks.

The fatigue reporter 152 can be configured to generate a customized force graph based on the muscle fatigue predictions or multiple muscle fatigue predictions generated by the fatigue detector 275. The customized force graph can be further described with respect to FIG. 10, which is discussed below. The customized force graph can be transmitted to an output device 280 and displayed on a graphical user interface (GUI) 285 of the output device 280. In some implementations, the output device 280 and/or the GUI 285 can be included in the compute device 116. The GUI 285 can include any screen, monitor, touchscreen, trackpad, keyboard, any peripherals, and/or any combination thereof. In some implementations, the fatigue reporter 152 can display any outputs of the torque module 144 and/or the force module 148 on the GUI 285 along with the customized force graph.

Figure 3:
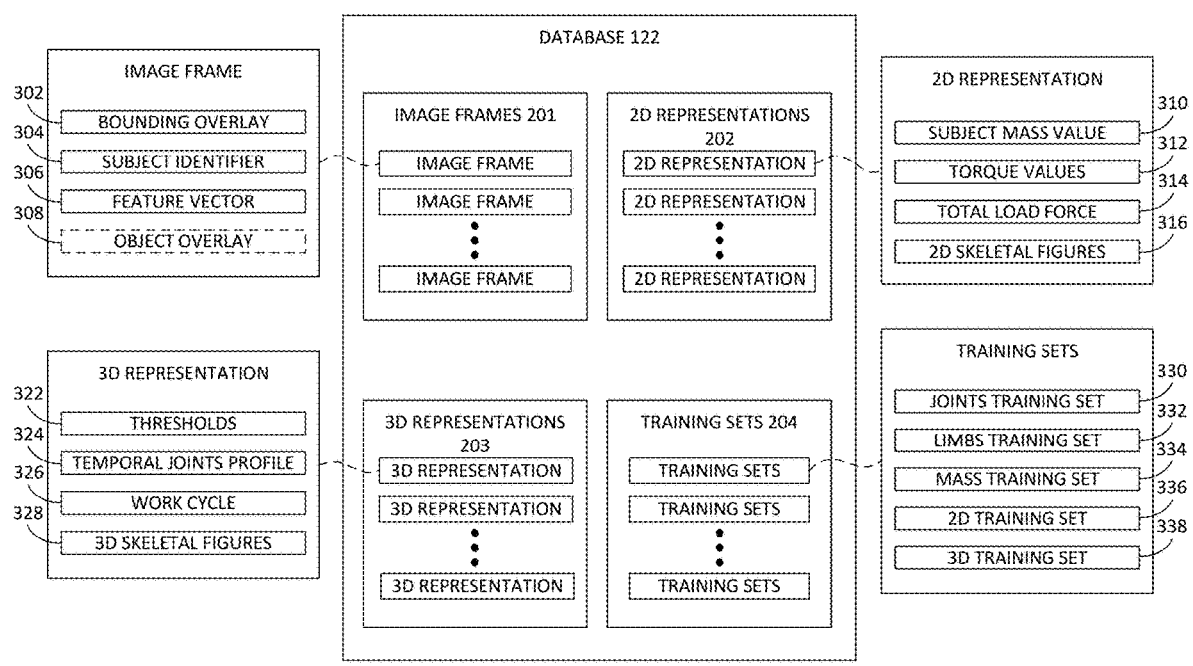
FIG. 3 is a block diagram of a database for calculating torque and force about body joints using machine learning to predict muscle fatigue, according to an embodiment.

FIG. 3 is a block diagram of a database for calculating torque and force about body joints using machine learning to predict muscle fatigue, according to an embodiment. The database can be the database 122 from FIG. 2, where the database 122 stores a list of image frames 201, a list of 2D representations 202, a list of 3D representations 203, and a list of training sets 204. The list of image frames 201 can include a sequence of individual image frames. The list of image frames 201 can depict a subject and/or multiple subjects. In some cases, the database 122 can store multiple lists of image frames and organize each list of image frames based on specific subjects depicted. Each image frame from the list of image frames 201 can include a bounding overlay 302, a subject identifier 304, a feature vector 306, and/or an object overlay 308. The bounding overlay 302 can be consistent with any bounding overlay as described herein. The bounding overlay 302 can include a virtual representation in the shape of a box that outlines the subject depicted in the image frame. In some cases, each image frame can include multiple bounding overlays outlining multiple subjects detected in each image frame. The bounding overlay can include, for example, temporal joint data of the subject including the dimensional location of a recognizable human subject as the location shifts following the movements (or location) of the human subject captured across the image frames 201. In some cases, the temporal joint data can include 2D coordinates of the corners of the bounding overlay 302 outlining the subject.

The subject identifier 304 can include a unique identifier for each subject detected in the image frame. The subject identifier 304 can include a combination of numbers and/or natural language characters specific to a subject. The subject identifier 304 can be assigned to the subject along with the bounding overlay 302 to identify and/or track the subject across the list of image frames 201 (and to reduce computational overhead).

The feature vector 306 (also referred to as "dimensional feature vector") can include measurable characteristics such as, for example, height of the subject, patterns associated with the subject, and/or numerical features describing the subject (e.g., 2D pixel locations and/or coordinates of the subject, parts of the subjects, the object, etc.). The feature vector 306 can also describe, for example, extracted features of the subject detected in the image frame including appearance. In some implementations, the feature vector 306 of an image frame can be used to track the subject for the bounding overlay 302.

The image frame can optionally include the object overlay 308. The object overlay 308 can include a virtual representation in a geometric shape similar to an object detected in the image frame. The object can be engaged by the user such as, for example, a box, a door, a forklift, a keyboard, or the like. The object can be detected and outlined by the object overlay 308 to be easily identified across the list of image frames 201. The object overlay 308 can also be assigned with an object identifier including a unique combination of numbers and natural language characters.

The database 122 can include the list of 2D representations where the list of 2D representations can include 2D representations of multiple subjects detected and/or multiple video inputs. The 2D representation can be consistent with any 2D representation as described herein. The 2D representation can include a subject mass value 310, torque values 312, total load force 314, and/or a set of 2D skeletal figures 316. The subject mass value 310 can include (or be) a mass/weight of the subject depicted in the 2D representation. The torque values 312 can include (or be) torque computed for each joint of the body of the subject across a sequence of image frames of the 2D representation. The total load force 314 (also referred to as "total force") can include (or be) a numerical value for an action exerted by the subject and/or exerted by the subject on an object. The action can include, for example, lifting, pushing, pulling, and/or any combination thereof. The 2D skeletal figures 316 can include a set of 2D skeletal figure, each 2D skeletal figure mimicking the subject detected in each image frame. The 2D skeletal figures 316 can be consistent with any 2D skeletal figures as described herein.

The database 122 can store the list of 3D representations 203, each 3D representation including thresholds 322, a temporal joints profile 324, an identification of a work cycle 326, and/or a set of 3D skeletal figures. The 3D representation can be consistent with any 3D representation as described herein. The thresholds 322 can include, for example, a fatigue threshold, including a torque threshold and a force threshold. Each 3D representation can be associated with the thresholds 322 as each 3D representation can be associated with a specific subject where the subject can be assigned with thresholds different from that of other subjects. For instance, a younger and fit subject can be associated with higher thresholds 322 than an older subject with a history of bodily injuries.

The 3D representation can include the set of 3D skeletal figures 328. In some implementations, each 3D skeletal figure can include a pointer identifying a corresponding 2D skeletal figure for an associated image frame from the list of image frames 201. The set of 3D skeletal figures can include a 3D reconstruction of the set of 2D skeletal figures 316. The set of 3D skeletal figures can depict, for example, a set of poses performed by the subject. In some cases, the 3D skeletal figure can also include a geometric representation of any object involved in an action performed by the subject. Each 3D skeletal figure can, for example, outline the set of joints and connecting limb segments (or body parts) of the subject depicted in each image frame. The 3D skeletal figure can be overlayed on the image frame, thereby producing an outline of the subject's skeletal framework on top of the subject depicted in the image frame. This is so, at least in part, to identify the subject's pose and/or movement in a sequence of time.

The 3D representation can also include the identification of a work cycle 326. The work cycle can be, for example, a time period in which the subject is performing a laboring action (e.g., lifting an object, pushing an object, pulling an object, etc.). The work cycle can also be associated with a subset of image frames from the list of image frames 201 where the subject is depicted laboring. For instance, the subject depicted in the list of image frames 201 can be taking a break for most of the image frames, while the remainder of image frames depicts the subject pushing a cart from one location to another. The image frame depicting the subject beginning to push the cart to the image frame depicting the subject finishing the pushing of the cart can be denoted as a work cycle. The work cycle can also be a sequence of poses including a beginning pose and an end pose depicting the start and finish of the subject completing a laboring action. The identification of the work cycle 326 from the 3D representation can also include 3D skeletal figures 328 for which the work cycle is present.

The 3D representation and/or the set of 3D skeletal figures can include a temporal joints profile 324 of a set of temporal joints profile. The temporal joints profile 324 can be, for example, a sequence of a joint from the list of 3D skeletal figures 328 depicting 3D poses of the subject based on the list of image frames 201. In an example, a temporal joints profile 324 for a right wrist can depict the 3D locations (e.g., 3D coordinates) of the right wrist in a 3D space by connecting the locations of the right wrist in each 3D skeletal figure associated with each image frame in the list of image frames 201. The 3D representation can include a complete set of temporal joints profiles for each joint of the body of the subject.

The list of training sets 204 can include multiple training sets used to train multiple machine learning models and/or neural networks of the compute device of FIG. 1 or FIG. 2. The training set from the list of training sets 204 can include a joints training set 330, a limbs training set 332, a mass training set 334, a 2D training set 336, and/or a 3D training set 338.

The joints training set 330 can be used, for example, to train the joints localizer of the 2D generator network of the skeletal figure engine of FIG. 2. The joints training set 330 can include image data correlated to joint localization data. The image data can include data describing the subject depicted and/or the bounding overlay 302. The joint localization data can include 2D locations and/or coordinates representing joints (or combination of joints). The joint location data can also include a heat map describing the 2D locations and/or coordinates of each joint of the subject.

The limbs training set 332 can be used to train the limbs localizer 232 of FIG. 2. The limbs training set 332 can include, for example, the joint localization data correlated to limb localization data. The limb localization data can include vectors representing limbs and/or body parts, unit vectors connecting two joints, and/or the like.

The mass training set 334 can be used to train the mass estimation network. The mass training set 334 can include, for example, image data correlated to mass data. The image data can include an identification of the subject, data describing the shape of the bounding overlay 302 surrounding the subject, data describing height, gender, and/or age of the subject, and/or the like. The mass data can include a subject mass value associated with a subject. The mass data can include multiple subject mass values associated with subjects classified by gender, height, build, age, ethnicity, and/or the like.

The 2D training set 336 can be used to train the 2D generator network of FIG. 2. The 2D training set 336 can include, for example, localization data correlated to 2D figure sequence data. The localization data can include, for example, data describing the joints of the body of the subject and body parts that connect between two joints and/or limbs protruding from one or more joints. The 2D figure sequence data can include, for example, data describing a 2D location and/or coordinates of a 2D skeletal figure and 2D location and/or coordinates of a sequence of 2D skeletal figures.

The 3D training set 338 can be used to train the 3D transformer network of FIG. 2. The 3D training set 338 can include, for example, a 2D figure sequence data correlated to 3D figure sequence data. The 3D figure sequence data can also include, for example, temporal joints data. The temporal joints data can include 3D locations and/or coordinates, unit vectors, and/or the like, of a path traveled by a joint of the subject in a 3D space.

Figure 4:
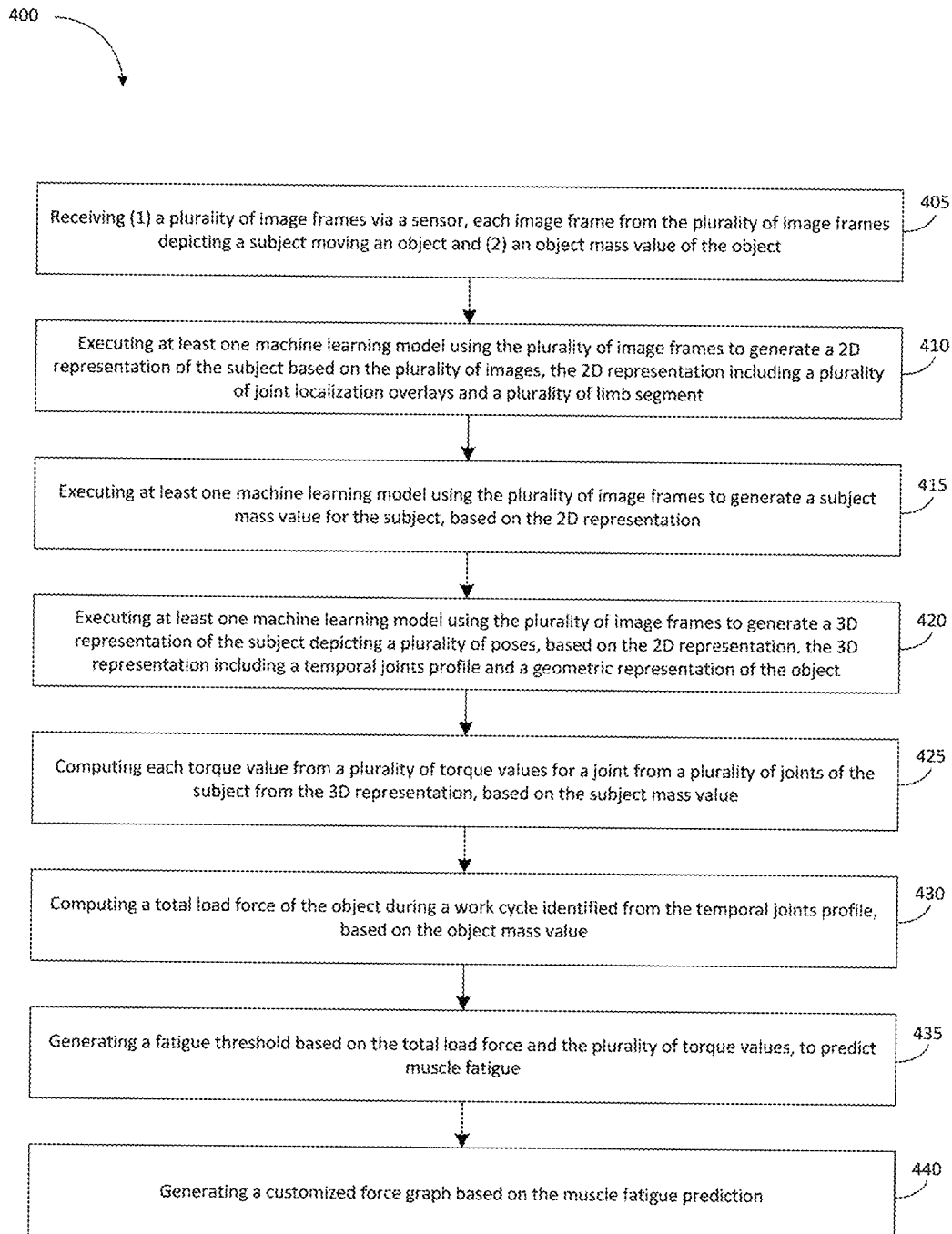
FIG. 4 is a flow diagram of a method for calculating torque and force about body joints using machine learning to predict muscle fatigue.

FIG. 4 is a flow diagram of a method 400 for calculating torque and force about body joints using machine learning to predict muscle fatigue. At 405, the method 400 includes receiving (1) a sequence of image frames via a sensor, each image frame from the sequence of image frames depicting a subject moving an object and (2) an object mass value of the object. The sensor can include any sensor(s) and/or camera (s) as described herein. The object mass value can be the mass/weight of the object.

In some implementations, the method 400 can include generating, via at least one machine learning model, a bounding overlay from a set of bounding overlays outlining the subject depicted in the sequence of image frames, based on the sequence of image frames. The at least one machine learning model can include (or be), for example, a convolutional neural network, a transformer neural network, a hybrid neural network, and/or any combination thereof. The bounding overlay in each image frame can include temporal joint data of the subject. The method 400 can also include generating, via the at least one, a dimensional feature vector from a set of dimensional feature vectors using the set of bounding overlays as an input. The method 400 can also include matching the set of bounding overlays outlining the subject across two or more image frames from the sequence of image frames by generating a set of feature vectors. In some cases, the method 400 can include executing a different machine learning model to generate bounding overlays and a different machine learning model to track the subject by matching the bounding overlays across the sequence of image frames.

In some implementations, the method 400 can include executing multiple machine learning models, neural networks, convolutional neural networks, hybrid neural networks, transformer neural networks, and/or any combination thereof. In some cases, the method 400 can include generating a subject identifier for the subject, based on the set of dimensional feature vectors and the set of bounding overlays. The subject identifier can be unique and associated with a specific subject to quickly identify the subject across different sequences of image frames. The subject identifier can also distinguish different subjects detected.

At 410, the method 400 includes executing the least one machine learning model using the sequence of image frames to generate a 2D representation of the subject. The 2D representation can include a set of joint localization overlays and a set of limb segments. The 2D representation can include a set of 2D skeletal figures where each 2D skeletal figures include a joint localization overlay formed by a set of identified joints, and a limb localization overlay formed by the set of limb segments connecting via the identified joints. In some cases, the method 400 can include executing another machine learning model to generate the joint localization overlay for each image fame. For example, the method 400 can also include executing another machine learning model to generate the limb localization overlay for each image frame. Another machine learning model can use a set of joint localization overlays and a set of limb localization overlays to generate the 2D representation.

At 415, the method 400 includes executing the at least one machine learning model using the sequence of image frames to generate a subject mass value for the subject, based on the 2D representation and/or the 3D representation. The subject mass value can include a mass/weight of the subject depicted in the 2D representation and/or the 3D representation. In some implementations, the method 400 can include generating multiple subject mass values for multiple subjects detected. In some implementations, the method 400 can include receiving, via user input, a center mass value for each limb segment of the subject, based on demographic data of the subject. A set of center mass value can be used to generate a body part mass for each body part including limbs of the subject.

At 420, the method 400 includes executing the at least one machine learning model using the sequence of image frames to generate a 3D representation of the subject. The 3D representation can depict a set of poses, based on the 2D representation. The 3D representation can be a temporal joints profile and a geometric representation of the object. The temporal joints profile can be generated, for example, based on the set of poses of a set of 3D skeletal figures of the 3D representation. In some implementations, the method 400 can include generating, via the at least one machine learning model, a set of frame interrelations using the 2D representation and a time sequence as inputs, to produce the 3D representation. The set of frame interrelations can include a sequence of the 3D poses of the set of 3D skeletal figures in a 3D space. The sequence of 3D poses can represent an action performed by the subject. In some implementations, generating the set of frame interrelations can include extracting a set of scaled frame interrelations based on a convolutional filter size prior to generating the 3D representation. This is so, at least in part, to reduce computational overhead in reconstructing the 2D representation into the 3D representation.

In some implementations, the method 400 can include generating a center mass value of each body part from the set of body parts of the subject based on the 3D representation of the subject. The method 400 can also include generating a body part model of the body part associated with the object. The body part model can include a representation of the body part and the geometric representation of the object. The geometric representation of the object can include, for example, a rectangular prism, a sphere, a cylinder, a cone, or the like, based on a shape of the object.

At 425, the method 400 includes computing each torque value from a set of torque values for a joint from a set of joints of the subject from the 3D representation, based on the subject mass value. In some implementations, the method 400 can include performing a numerical differentiation on the 3D representation to produce a linear acceleration value and an angular acceleration value for each limb segment from the set of limb segments of the subject, to compute each torque value from the set of torque values. In some cases, computing the set of torque values can include computing the moment of inertia about each joint caused by the body part of the object that is engaged with the subject.

At 430, the method 400 includes computing a total load force of the object during the work cycle identified from the temporal joints profile, based on the object mass value. Computing the total load force of the object includes computing the total load force exerted by the subject and/or exerted by the subject and on the object when performing an action such as, for example, lifting, pushing, pulling, or the like.

At 435, the method 400 includes generating a fatigue threshold based on the total load force and the plurality of torque values, to predict muscle fatigue. The method 400 can include detecting the work cycle based on the temporal joints profile of the set of temporal joints profile of the 3D representation for the subject. The work cycle can include, for example, a beginning pose and an ending pose from the set of poses for an action performed by the subject. The method 400 can also include detecting a time sequence of the work cycle, to generate the muscle fatigue prediction of the subject during the time sequence associated with the work cycle.

At 440, the method 400 includes generating a customized force graph based on the muscle fatigue prediction. The method 400 can include, for example, displaying the customized force graph on an output device.

Figure 5:
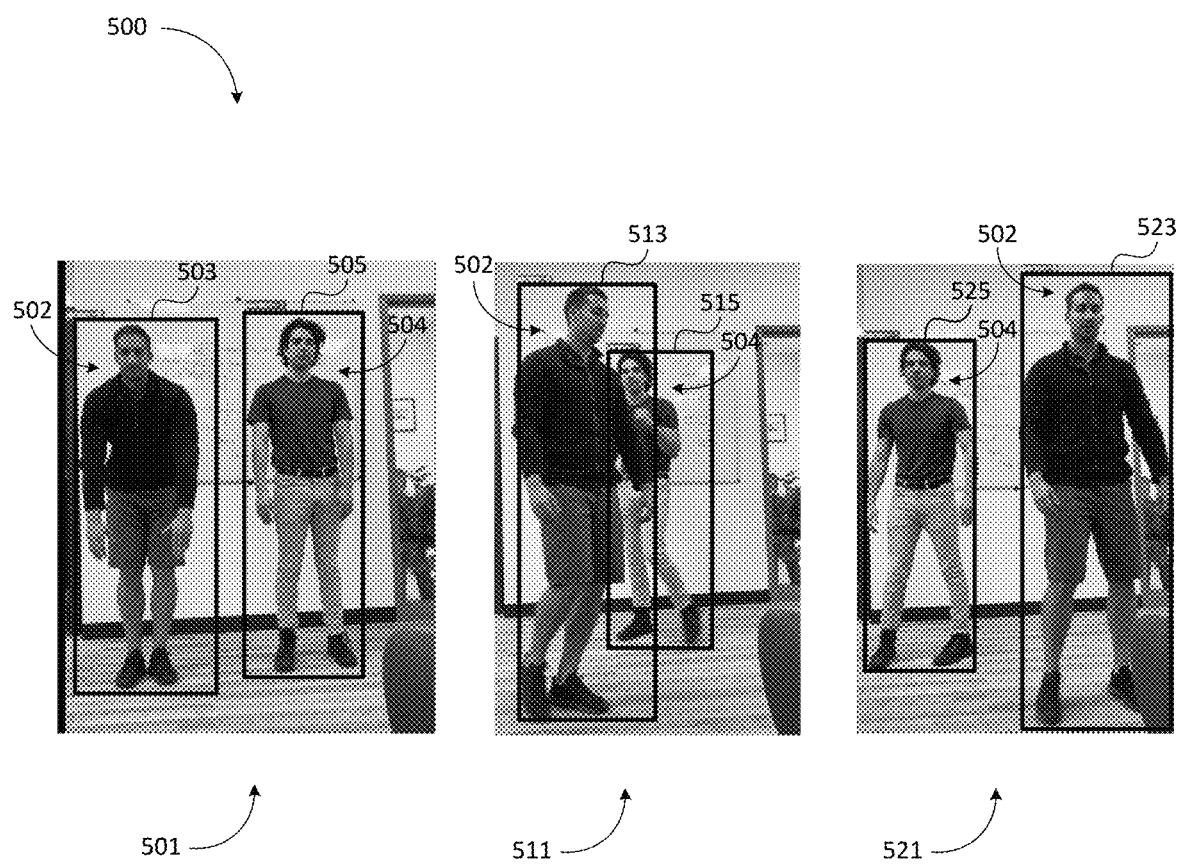
FIG. 5 is schematic illustration for detecting a set of subjects and tracking the set of subject across frames, according to an embodiment.

FIG. 5 illustrates a schematic illustration for detecting a set of subjects and tracking the set of subject across frames, according to an embodiment. FIG. 5 shows a sequence of image frames 500 captured from a camera at a position. Each image frame depicts multiple subjects. In a first image frame 501, a first subject 502 and a second subject 504 are depicted. A machine learning model can detect the first subject 502 and the second subject 504. In some implementations, another machine learning model can generate a first bounding overlay 503 and a second bounding overlay 505 outlining the first subject 502 and the second subject 504, respectively. The bounding overlays 503 and 505 can include a virtual representation of a box that surrounds each respective subject individually. Each bounding overlay 503 and 505 can be shaped to outline a subject (e.g., the first subject 502 and the second subject 504) based on the subject's height and/or size. Each bounding overlay 503 and 505 can also be associated with a subject identifier distinguishing multiple subjects (e.g., the first subject 502 and the second subject 504).

A second image frame 511 depicts the first subject 502 and the second subject 504 at different locations. As shown in FIG. 5, the first subject 502 is closer to the camera and the second subject 504 is located partially behind the first subject 502 and further from the camera. Another machine learning model can track the location of each subject using each subject's bounding overlay and/or subject identifier. As shown in FIG. 5, the second image frame 511 can include a new set of bounding overlays for each subject. A first bounding overlay 513 outlines the first subject 502 in the second image frame 511 and a second bounding overlay 515 outlines the second subject 504. The first bounding overlay 513 of the second image frame 511 can be larger than the first bounding overlay 503 of the first image frame 501 as the first subject 502 appears larger in the second image frame 511 than in the first image frame 501. The second bounding overlay 515 of the second image frame 511 can overlap with the first bounding overlay 513 of the second image frame 511 and be smaller than the second bounding overlay 505 of the first image frame 501, as the second subject 504 is located partially behind the first subject 502 as depicted in the second image frame 511.

At a third image frame 521, the first subject 502 is located at a right side of the third image frame 521 and the second subject 504 is located at a left side of the third image frame 521. As shown in FIG. 5, the first subject 502 and the second subject 504 switched locations. A first bounding overlay 523 in the third image frame 521 outlines the first subject 502 and a second bounding overlay 525 in the third image frame 521 outlines the second subject 504 accordingly. Each subject is tracked across the sequence of image frames 500 and as such, each subject's respective bounding overlays follows its respective subject across the sequence of image frames 500.

Figure 6:
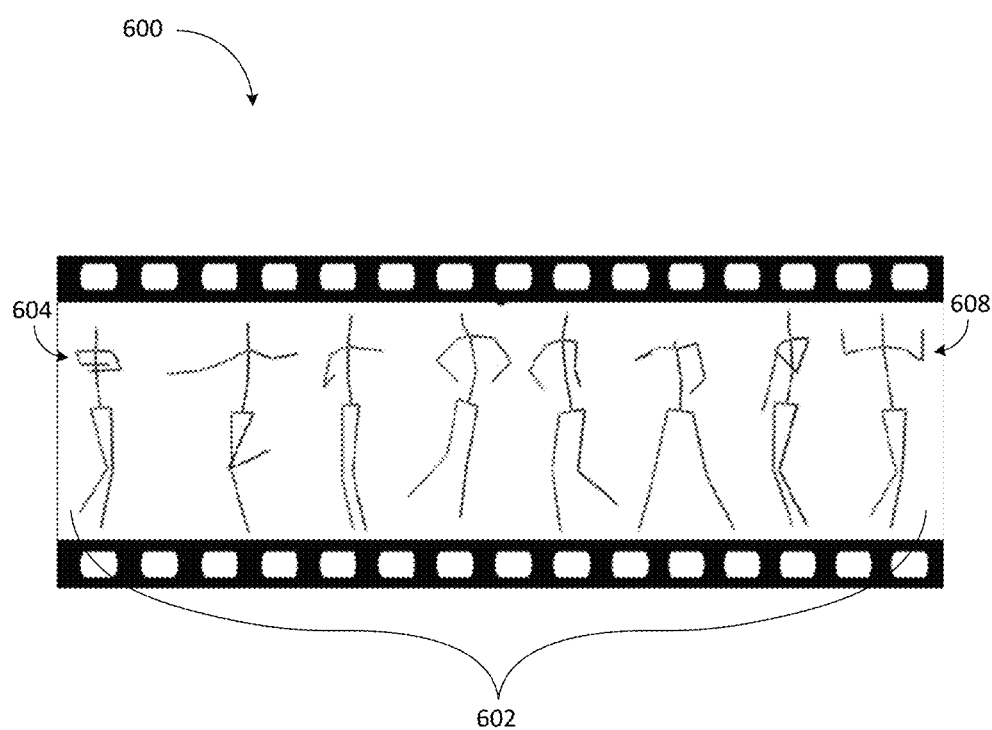
FIG. 6 is a sequence of 2D skeletal figures forming a 2D representation depicting a subject, according to an embodiment.
Figure 7:
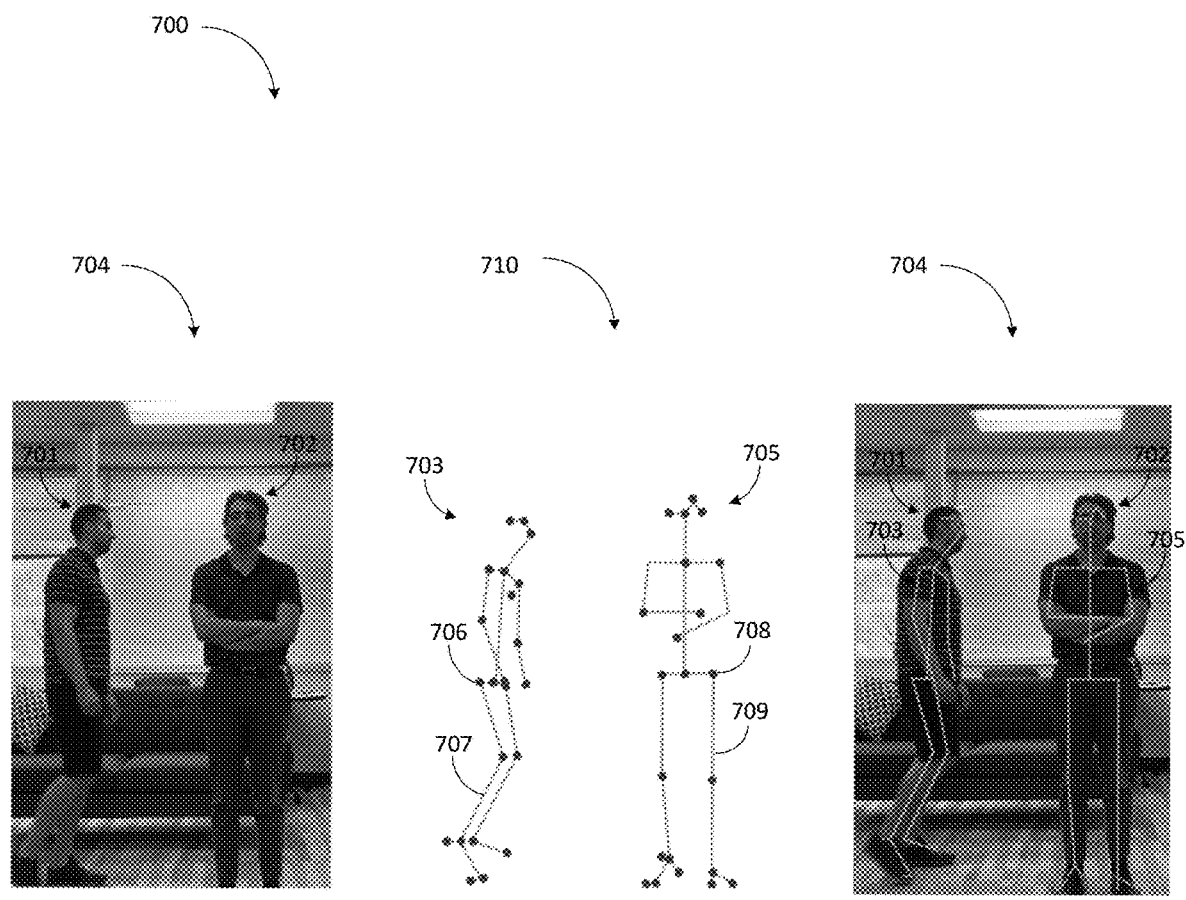
FIG. 7 is a set of image frames including 2D skeletal figures overlayed on each subject in the set of image frames, according to an embodiment.

FIG. 6 illustrates a sequence of 2D skeletal figures 602 forming a 2D representation 600 depicting a subject, according to an embodiment. The 2D representation 600 includes the sequence of 2D skeletal figures 602 where each 2D skeletal figure is a reconstructed representation of a subject depicted in each image frame from a sequence of image frames. Each 2D skeletal figure depicts a pose of the subject while performing an action, such as, for example, lifting, pushing, carrying pulling, or the like. The 2D representation 600 also include the sequence of 2D skeletal figures 602 where each 2D skeletal figure depicts a 2D pose (or pose). A first pose 604 from the sequence of 2D skeletal figures 602 to a last pose 608 from the sequence of 2D skeletal figures 602 and can denote a work cycle.

FIG. 7 illustrates a set of image frames 700 including 2D skeletal figures 710 overlayed on each subject in the set of image frames 700, according to an embodiment. An image frame 704 depicts a first subject 701 and a second subject 702. The first subject 701 is facing to the right and the second subject 702 is facing to the front. A machine learning model can generate, based on the image frame, a set of 2D skeletal figures 710 for each subject detected in the image frame 704 (e.g., the first subject 701 and the second subject 702).

The set of 2D skeletal figures 710 can be associated with the image frame 704. In some instances, each image frame from a sequence of image frames can include its own 2D skeletal figure and/or set of 2D skeletal figures for a subject and/or multiple subjects depicted in each image frame. The set of 2D skeletal figures 710 can include a first 2D skeletal FIG. 703 associated with the first subject 701 and a second 2D skeletal FIG. 705 associated with the second subject 702. A 2D skeletal figure can be a simplified reconstruction of a subject where the 2D skeletal figure includes a combination of vectors and points depicting body parts and joints, respectively. The 2D skeletal figure can also mimic a pose of the subject. The first 2D skeletal FIG. 703 can include a set of joints 706 and a set of body parts 707. The set of body parts 707 can include, for example, limbs. The second 2D skeletal FIG. 705 represents the second subject 703. The second 2D skeletal figure can include a set of joints 708 and a set of body parts 709 (or set of limbs).

Once the set of 2D skeletal figures 710 are constructed, the set of 2D skeletal figures 710 can be overlayed on the associated image frame 704 as shown in FIG. 7. The first subject 701 includes an overlay of the first 2D skeletal FIG. 703 and the second subject 702 includes an overlay of the second 2D skeletal FIG. 705.

Figure 8:
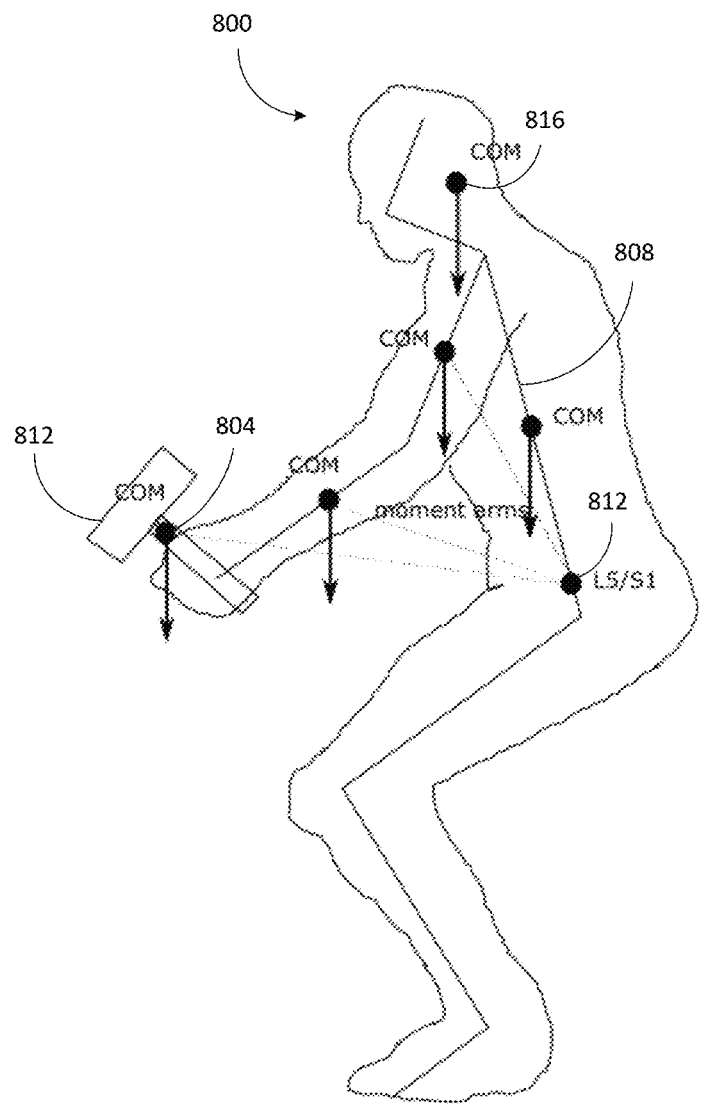
FIG. 8 is a schematic illustration of a human subject holding an object and a 2D representation depicting a set of center of masses, according to an embodiment.

FIG. 8 is a schematic illustration of a human subject 800 holding an object 812 and a 2D representation 808 depicting a set of center of masses 816, according to an embodiment. FIG. 8 also shows a center of mass for the object 812 (e.g., object center mass 804). The set of center of masses 816, the object 812, and/or the object center mass 804 can be used to determine static load on a joint from a set of joints, such as a back joint 812 (L5/S1 lumbosacral joint).

Figure 9:
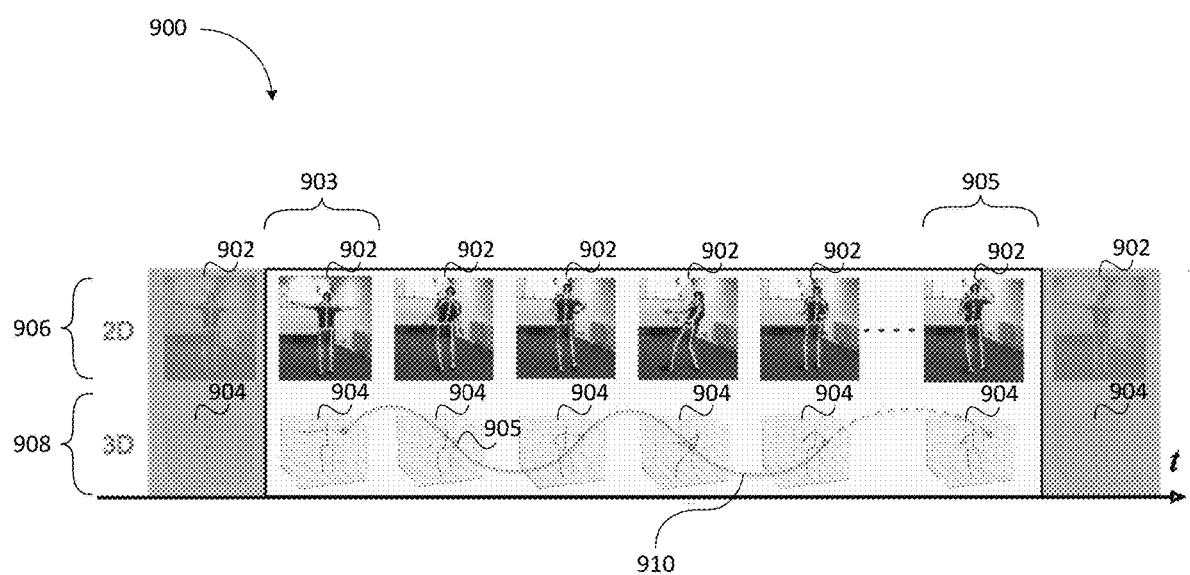
FIG. 9 is a schematic illustration of a 2D sequence of poses and a 3D sequence of poses including a temporal joints profile, according to an embodiment.

FIG. 9 is a schematic illustration 900 of a 2D sequence of poses and a 3D sequence of poses including a temporal joints profile 910, according to an embodiment. The illustration 900 depicts a 2D representation 906 that includes 2D sequence of poses where the 2D sequence of poses includes a sequence of image frames with a set of 2D skeletal figures overlayed on the sequence of image frames. Each image frame 902 includes a 2D skeletal figure overlayed on a subject. In some cases, the 2D sequence of poses can also refer to as a 2D representation.

The schematic illustration 900 also depicts a 3D representation 908 including the 3D sequence of poses. The 3D sequence of poses can include a set of 3D skeletal figures 904 in a 3D space. Each 3D skeletal figure can be correlated with a 2D skeletal figure. As such, each image frame can be associated with a specific 2D skeletal figure and a 3D skeletal figure. In the sequence of image frames, the subject can be depicted to perform an action (e.g., lifting, pulling, pushing, etc.). The beginning of the action can be denoted as a beginning pose 903 and the ending of the action can be denoted as an end pose 905. The beginning pose 903 can include an image frame and an associated 2D skeletal figure and associated 3D skeletal FIG. 904. The beginning pose 903 can denote a beginning of a work cycle, i.e., the start of a laboring action, and the end pose 905 can denote an ending of the work cycle, i.e., the end of the laboring action.

The 3D representation 908 can also include the temporal joints profile 910. The temporal joints profile 910 can be a sequence of a joint of interest 905 from a sequence of 3D skeletal figures depicting 3D poses of the subject based on the sequence of image frames. The temporal joints profile 910 can also include a path traveled by a joint in the 3D space. In some cases, the temporal joints profile 910 can begin from the beginning of the work cycle and end at the ending of the work cycle. In some cases, the 3D representation can include a complete set of temporal joints profiles for each joint of the subject.

Figure 10A:
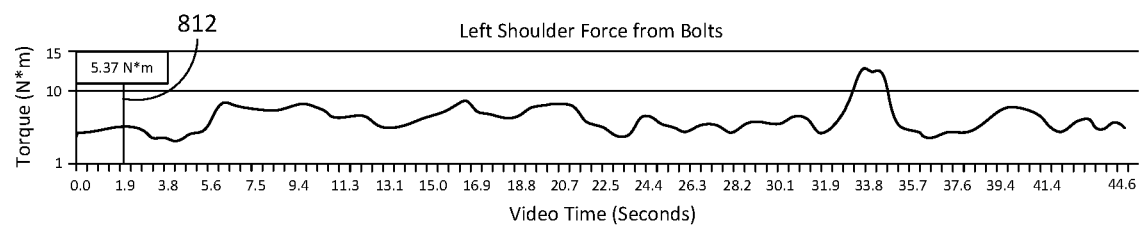
FIG. 10A-B is a schematic illustration of a graph depicting muscle fatigue for a left shoulder and a right shoulder, respectively, according to an embodiment.
Figure 10B:
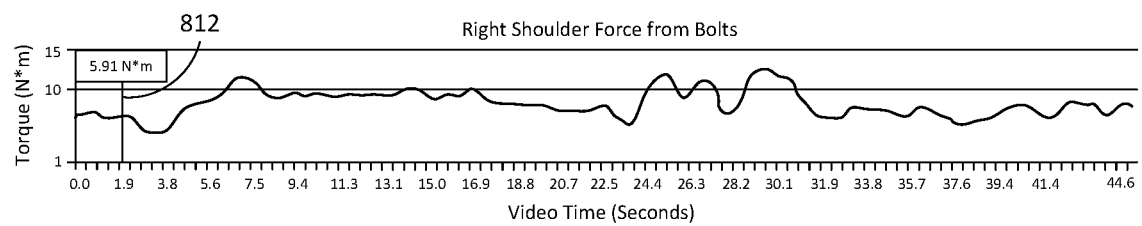

FIG. 10A-B is a schematic illustration of a graph depicting muscle fatigue for a left shoulder and a right shoulder, respectively, according to an embodiment. FIG. 10A shows a graph depicting force applied by the left shoulder and FIG. 10B shows a graph depicting force applied by the right shoulder. In some implementations, the graphs depicted in FIG. 10A-B can be modeled as Torque (N*m) over time as represented as the Y-axis. A current time can be obtained via a current video frame and/or a frames per second of the video, where time in seconds is represented as the X-axis. The graph in FIG. 10A depicts the force applied for the left shoulder engaged with an object (or objects) such as bolts. The graph in FIG. 10B depicts the force applied for the right shoulder engaged with an object (or objects) such as bolts.

In some implementations, an object mass value can be provided to generate the graphs. The object mass value can be any number greater than zero and can be for example in units of pounds. In some cases, the number can be converted to metric units for calculations. A user can also provide a user input indicating which hand(s) was used to engage with the object. User inputs can include left hand, right hand, or both hands. In some cases, the user input can be used to compute a set of torque values and/or a total load force as described in FIG. 2, to generate the graphs shown in FIG. 10A or FIG. 10B.

In some implementations, the graphs displayed on an output device (e.g., a display of a compute device such as compute device 116 of FIG. 1) can be interactive via a GUI. For instance, the user can drag a line 812 to skip ahead in the video to a second time and view the torque value at the second time. The calculation of the torque value in the Y-axis can be synced with the line 812.

It is to be noted that any one or more of the aspects and embodiments described herein can be conveniently implemented using one or more machines (e.g., one or more compute devices that are utilized as a user compute device for an electronic document, one or more server devices, such as a document server, etc.). programmed according to the teachings of the present specification. Appropriate software coding can readily be prepared by skilled programmers based on the teachings of the present disclosure. Aspects and implementations discussed above employing software and/or software modules can also include appropriate hardware for assisting in the implementation of the machine executable instructions of the software and/or software module.

Such software can be a computer program product that employs a machine-readable storage medium. A machine-readable storage medium can be any medium that is capable of storing and/or encoding a sequence of instructions for execution by a machine (e.g., a compute device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software can also include information (e.g., data) carried as a data signal on a data carrier, such as a carrier wave. For example, machine-executable information can be included as a data-carrying signal embodied in a data carrier in which the signal encodes a sequence of instruction, or portion thereof, for execution by a machine (e.g., a compute device) and any related information (e.g., data structures and data) that causes the machine to perform any one of the methodologies and/or embodiments described herein.

Examples of a compute device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a compute device can include and/or be included in a kiosk.

All combinations of the foregoing concepts and additional concepts discussed herewithin (provided such concepts are not mutually inconsistent) are contemplated as being part of the subject matter disclosed herein. The terminology explicitly employed herein that also can appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein can be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments can be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments cannot have been presented for a specific portion of the innovations or that further undescribed alternate embodiments can be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments can be utilized and functional, logical, operational, organizational, structural and/or topological modifications can be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For example, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general-purpose processor, a central processing unit (CPU), a microprocessor, a digital signal processor (DSP), a controller, a microcontroller, a state machine and so forth. Under some circumstances, a "processor" can refer to an application specific integrated circuit (ASIC), a programmable logic device (PLD), a field programmable gate array (FPGA), etc. The term "processor" can refer to a combination of processing devices, e.g., a combination of a DSP and a microprocessor, multiple microprocessors, one or more microprocessors in conjunction with a DSP core or any other such configuration.

The term "memory" should be interpreted broadly to encompass any electronic component capable of storing electronic information. The term memory can refer to various types of processor-readable media such as random-access memory (RAM), read-only memory (ROM), non-volatile random-access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" can refer to one or more programs, routines, sub-routines, functions, procedures, etc. "Instructions" and "code" can comprise a single computer-readable statement or many computer-readable statements.

The term "module" can be, for example, distinct but interrelated units from which a program may be built up or into which a complex activity may be analyzed. A module can also be an extension to a main program dedicated to a specific function. A module can also be code that is added in as a whole or is designed for easy reusability.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules can include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.). or other suitable programming languages and/or development tools. Additional examples of computer code include, but are not limited to, control signals, encrypted code, and compressed code.

Various concepts can be embodied as one or more methods, of which at least one example has been provided. The acts performed as part of the method can be ordered in any suitable way. Accordingly, embodiments can be constructed in which acts are performed in an order different than illustrated, which can include performing some acts simultaneously, even though shown as sequential acts in illustrative embodiments. Put differently, it is to be understood that such features can not necessarily be limited to a particular order of execution, but rather, any number of threads, processes, services, servers, and/or the like that can execute serially, asynchronously, concurrently, in parallel, simultaneously, synchronously, and/or the like in a manner consistent with the disclosure. As such, some of these features can be mutually contradictory, in that they cannot be simultaneously present in a single embodiment. Similarly, some features are applicable to one aspect of the innovations, and inapplicable to others.

In addition, the disclosure can include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein can be implemented in a manner that enables a great deal of flexibility and customization as described herein.

All definitions, as defined and used herein, should be understood to control over dictionary definitions, definitions in documents incorporated by reference, and/or ordinary meanings of the defined terms.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
a processor; and
a memory operatively coupled to the processor, the memory storing instructions to cause the processor to:
receive a plurality of image frames, each image frame from the plurality of image frames depicting a subject;
execute at least one machine learning model using the plurality of image frames as an input, to generate:
a 2D representation of the subject based on the plurality of image frames, the 2D representation including a plurality of joint localization overlays and a plurality of limb segments,
a subject mass value for the subject based on the 2D representation, and
a 3D representation of the subject based on the 2D representation, the 3D representation including a temporal joints profile;
compute each torque value from a plurality of torque values for a joint from a plurality of joints of the subject from the 3D representation based on the subject mass value;
detect a work cycle based on the temporal joints profile of the 3D representation, the work cycle including a beginning pose and an ending pose of an action performed by the subject; and
detect a time sequence of the work cycle, to generate a muscle fatigue prediction for each joint from the plurality of joints of the subject during the time sequence associated with the work cycle based on the plurality of torque values and a torque threshold.

2. The apparatus of claim 1, wherein the memory stores instructions to cause the processor to generate a bounding overlay from a plurality of bounding overlays outlining the subject in the plurality of image frames prior to generating the 2D representation, the bounding overlay including temporal joint data of the subject.

3. The apparatus of claim 2, wherein the memory stores instructions to cause the processor to generate a subject identifier for the subject, based on the plurality of dimensional feature vectors and the plurality of bounding overlays, to identify the subject in new image frames.

4. The apparatus of claim 1, wherein the memory stores instructions to cause the process to execute the at least one machine learning model to:
generate a dimensional feature vector from a plurality of dimensional feature vectors using a plurality of bounding overlays as an input, the plurality of bounding overlays outlining the subject in the plurality of image frames prior to generating the 2D representation; and
match the plurality of bounding overlays outlining the subject across two or more image frames from the plurality of image frames by generating a plurality of feature vectors.

5. The apparatus of claim 1, wherein the at least one machine learning model includes a convolutional neural network.

6. The apparatus of claim 1, wherein the at least one machine learning model includes an unsupervised machine learning model.

7. The apparatus of claim 1, wherein the instructions to cause the processor to execute the at least one machine learning model to generate the 2D representation includes instructions to cause the processor to:
generate the plurality of joint localization overlays using the plurality of image frames as an input, the plurality of joint localization overlays including a map of the plurality of joints of the subject across the plurality of image frames; and
generate a plurality of limb localization overlays using the plurality of joint localization overlays as an input, the plurality of limb localization overlays including a map of the plurality of joints and the plurality of limb segments connecting each joint of the plurality of joints of the subject across the plurality of image frames, to produce the 2D representation.

8. The apparatus of claim 1, wherein the instructions to cause the processor to execute the at least one machine learning model to generate the 3D representation includes instructions to cause the processor to:
generate a plurality of frame interrelations using the 2D representation and the time sequence as inputs, to produce the 3D representation, the plurality of frame interrelations including a sequence of the 3D poses in a 3D space.

9. The apparatus of claim 1, wherein the memory further stores instructions to cause the processor to perform numerical differentiation on the 3D representation to produce a linear acceleration value and an angular acceleration value for each limb segment from the plurality of limb segments of the subject, to compute each torque value from the plurality of torque values.

10. An apparatus, comprising:
a processor; and
a memory operatively coupled to the processor, the memory storing instructions to cause the processor to:
receive a plurality of image frames, each image frame from the plurality of image frames depicting a subject;
execute at least one machine learning model using the plurality of image frames as an input, to generate:
a 2D representation of the subject based on the plurality of image frames, the 2D representation including a plurality of joint localization overlays and a plurality of limb segments,
a subject mass value for the subject based on the 2D representation; and
a plurality of frame interrelations using the 2D representation and a time sequence as inputs, (1) to generate a 3D representation of the subject based on the 2D representation, and (2) extract a plurality of scaled frame interrelations based on a convolutional filter size prior to generating the 3D representation, the 3D representation including a temporal joints profile, the plurality of frame interrelations including a sequence of the 3D poses in a 3D space;
compute each torque value from a plurality of torque values for a joint from a plurality of joints of the subject from the 3D representation based on the subject mass value; and
generate a muscle fatigue prediction for each joint from the plurality of joints of the subject based on the plurality of torque values and a torque threshold,
the instructions to generate the plurality of frame interrelations include instructions to cause the processor to extract a plurality of scaled frame interrelations based on a convolutional filter size prior to generating the 3D representation.

11. An apparatus, comprising:
a processor; and
a memory operatively coupled to the processor, the memory storing instructions to cause the processor to:
receive (1) a plurality of image frames via a sensor, each image frame from the plurality of image frames depicting a subject moving an object and (2) an object mass value of the object;
execute at least one machine learning model using the plurality of image frames as an input, to generate:
a 2D representation of the subject based on the plurality of image frames, the 2D representation including a plurality of joint localization overlays and a plurality of limb segments; and
a 3D representation of the subject depicting a plurality of poses based on the 2D representation, the 3D representation including a temporal joints profile and a geometric representation of the object;
compute a total load force of the object during an action identified from the plurality of poses, based on the 3D representation and the object mass value; and
generate a muscle fatigue prediction for the subject based on the total load force of the object and a force threshold.

12. The apparatus of claim 11, wherein the memory further stores instructions to cause the processor to receive a center mass value of each limb segment from the plurality of limb segments of the subject, based on demographic data of the subject, to generate a body part mass for each body part from a plurality of body parts of the subject.

13. The apparatus of claim 11, wherein the memory further stores instructions to cause the processor to generate a center mass value of each body part from a plurality of body parts of the subject based on the 3D representation of the subject.

14. The apparatus of claim 11, wherein the memory stores instructions to further cause the processor to:
detect a center mass value of a body part associated with the object based on the 3D representation of the subject; and
generate a body part model of the body part associated with the object, the body part model including a representation of the body part and the geometric representation of the object.

15. The apparatus of claim 11, wherein the geometric representation of the object includes a rectangular prism, a sphere, a cylinder, or a cone based on a shape of the object.

16. A non-transitory, processor-readable medium storing processor-executable instructions to cause the processor to:
receive (1) a plurality of image frames via a sensor, each image frame from the plurality of image frames depicting a subject moving an object and (2) an object mass value of the object;
execute at least one machine learning model using the plurality of image frames as an input, to generate:
a 2D representation of the subject based on the plurality of image frames, the 2D representation including a plurality of joint localization overlays and a plurality of limb segments;
a subject mass value for the subject based on the 2D representation; and
a 3D representation of the subject depicting a plurality of poses based on the 2D representation, the 3D representation including a temporal joints profile and a geometric representation of the object;
compute each torque value from a plurality of torque values for a joint from a plurality of joints of the subject from the 3D representation, based on the subject mass value;
compute a total load force of the object during a work cycle identified from the temporal joints profile, based on the object mass value;
generate a fatigue threshold based on the total load force and the plurality of torque values, to predict muscle fatigue; and
generate a customized force graph based on the muscle fatigue.

17. The non-transitory, processor-readable medium of claim 16, wherein the non-transitory, processor-readable medium stores instructions to cause the processor to generate a plurality of fatigue thresholds for a plurality of repetitive actions performed by the subject.

18. The non-transitory, processor-readable medium of claim 16, wherein the non-transitory, processor-readable medium stores instructions to cause the processor to:
detect the work cycle based on the temporal joints profile of the 3D representation, the work cycle including a beginning pose and an ending pose of an action performed by the subject; and detect a time sequence of the work cycle, to generate the muscle fatigue prediction of the subject during the time sequence associated with the work cycle.

19. The non-transitory, processor-readable medium of claim 16, wherein the at least one machine learning model includes a convolutional neural network, a transformer neural network, or a hybrid neural network.

* * * * *

UNITED STATES PATENT AND TRADEMARK OFFICE
CERTIFICATE OF CORRECTION

PATENT NO. : 11,783,495 B1
APPLICATION NO. : 17/972796
DATED : October 10, 2023
INVENTOR(S) : Mitchell Messmore et al.

Page 1 of 1

It is certified that error appears in the above-identified patent and that said Letters Patent is hereby corrected as shown below:

In the Specification

Column 25, Lines 29-30: "FIG. 703 associated with the first subject 701 and a second 2D skeletal FIG. 705 associated with the second subject 702." should read -- figure 703 associated with the first subject 701 and a second 2D skeletal figure 705 associated with the second subject 702. --

Column 25, Line 35: "subject. The first 2D skeletal FIG. 703 can include a set of" should read -- subject. The first 2D skeletal figure 703 can include a set of --

Column 25, Line 38: "FIG. 705 represents the second subject 703. The second 2D" should read -- figure 705 represents the second subject 703. The second 2D --

Column 25, Line 44: "subject 701 includes an overlay of the first 2D skeletal FIG." should read -- subject 701 includes an overlay of the first 2D skeletal figure. --

Column 25, Line 46: "second 2D skeletal FIG. 705." should read -- second 2D skeletal figure 705. --

Column 26, Line 10: "and associated 3D skeletal FIG. 904. The beginning pose" should read -- and associated 3D skeletal figure 904. The beginning pose --

Signed and Sealed this
Fourteenth Day of November, 2023

Katherine Kelly Vidal
*Director of the United States Patent and Trademark Office*